US012780908B2

(12) United States Patent
Beachy et al.

(10) Patent No.: US 12,780,908 B2
(45) Date of Patent: Nov. 3, 2026

(54) POTENT ANTIGEN-BINDING DOMAINS THAT BIND PATCHED1 FOR ACTIVATION OF THE HEDGEHOG SIGNALING PATHWAY

(71) Applicant: The Board of Trustees of the Leland Stanford Junior University, Stanford, CA (US)

(72) Inventors: Philip A. Beachy, Stanford, CA (US); Yunxiao Zhang, La Jolla, CA (US); Aashish Manglik, Menlo Park, CA (US); Wan-Jin Lu, Redwood City, CA (US); Shuo Han, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 689 days.

(21) Appl. No.: 18/026,546

(22) PCT Filed: Sep. 27, 2021

(86) PCT No.: PCT/US2021/052192

§ 371 (c)(1),
(2) Date: Mar. 15, 2023

(87) PCT Pub. No.: WO2022/067178

PCT Pub. Date: Mar. 31, 2022

(65) Prior Publication Data

US 2023/0391861 A1 Dec. 7, 2023

Related U.S. Application Data

(60) Provisional application No. 63/083,544, filed on Sep. 25, 2020.

(51) Int. Cl.

| | |
|---|---|
| ***A61K 39/395*** | (2006.01) |
| ***C07K 14/39*** | (2006.01) |
| ***C07K 16/22*** | (2006.01) |
| ***C12N 15/70*** | (2006.01) |
| *A61K 38/00* | (2006.01) |

(52) U.S. Cl.

CPC .............. *C07K 16/22* (2013.01); *C07K 14/39* (2013.01); *C12N 15/70* (2013.01); *A61K 38/00* (2013.01); *C07K 2317/24* (2013.01); *C07K 2317/569* (2013.01); *C07K 2319/02* (2013.01); *C07K 2319/03* (2013.01)

(58) Field of Classification Search

None

See application file for complete search history.

(56) References Cited

U.S. PATENT DOCUMENTS

| | | | |
|---|---|---|---|
| 2013/0137856 | A1 | 5/2013 | Steyaert et al. |
| 2015/0093336 | A1 | 4/2015 | Van Ginderachter et al. |

OTHER PUBLICATIONS

De Marco et al. (2020) "Recombinant expression of nanobodies and nanobody-derived immunoreagents", Protein Expression and Purification, Apr. 11, 2020, vol. 172, 105645.

Federico et al. (2015) "Design of Decorin-Based Peptides That Bind to Collagen I and their Potential as Adhesion Moieties in Biomaterials", Angewandte Chemie International Edition, 2015, vol. 54, p. 10980-1 0984.

Zhang et al. (2019) "Hedgehog pathway activation through conformational blockade of the Patched sterol conduit". *bioRxiv*, pp. 1-46, 783290.

Zhang et al. (2019) "*Structure and Function of the Hedgehog Receptor Patched.*" Dissertation, pp. 1-172.

Zhang (2019) "Structure and function of the hedgehog receptor patched," Stanford Digital Repository, pp. 1-172, https://purl.stanford.edu/td405kg1904.

Barbeito et al. (2020) "HTR6 and SSTR3 ciliary targetng relies on both IC3 loops and C-terminal tails," bioRxiv, Life Science Alliance, https://doi.org/10.26508/lsa.202000746 vol 4 | No. 3, e202000746, pp. 1-24.

Zhang et al. (2020) "Hedgehog pathway activation through nanobody-mediated conformational blockade of the Patched sterol conduit," Proc Natl A cad Sci USA, vol. 117, pp. 28838-28846.

*Primary Examiner* — Christine J Saoud

(74) *Attorney, Agent, or Firm* — Pamela J. Sherwood; Bozicevic, Field & Francis LLP

(57) ABSTRACT

Provided is a conformation-specific antigen binding domain (ABD) specific for the Hedgehog receptor Patched1, which may be provided in the form of a nanobody. This nanobody potently activates the Hedgehog pathway in vitro and in vivo by stabilizing an alternative conformation of a Patched1 "switch helix". This ABD or nanobody is water soluble, i.e. does not require lipid modifications for its activity, facilitating mechanistic studies of Hedgehog pathway activation and therapeutic use.

8 Claims, 15 Drawing Sheets

Specification includes a Sequence Listing.

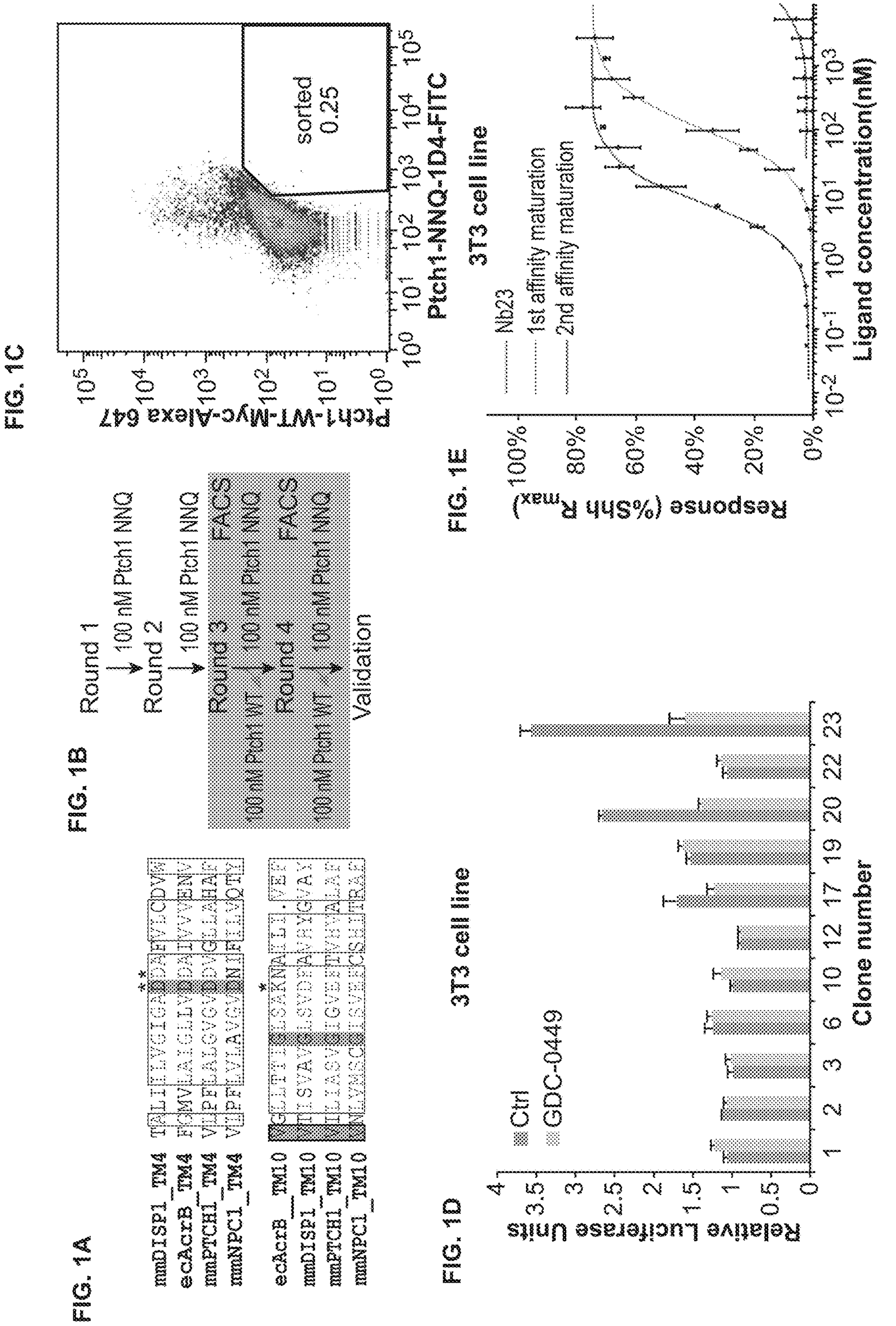
FIG. 1A
mmDISP1_TM4
ecAcrB_TM4
mmPTCH1_TM4
mmNPC1_TM4
ecAcrB_TM10
mmDISP1_TM10
mmPTCH1_TM10
mmNPC1_TM10
FIG. 1B
Round 1
100 nM Ptch1 NNQ
Round 2
100 nM Ptch1 NNQ
Round 3
100 nM Ptch1 WT
100 nM Ptch1 NNQ
FACS
Round 4
100 nM Ptch1 WT
100 nM Ptch1 NNQ
FACS
Validation
FIG. 1C
Ptch1-WT-Myc-Alexa 647
Ptch1-NNQ-1D4-FITC
sorted
0.25
FIG. 1D
3T3 cell line
Ctrl
GDC-0449
Relative Luciferase Units
Clone number
FIG. 1E
3T3 cell line
Nb23
1st affinity maturation
2nd affinity maturation
Response (%Shh $R_{max}$)
Ligand concentration(nM)

FIG. 3A
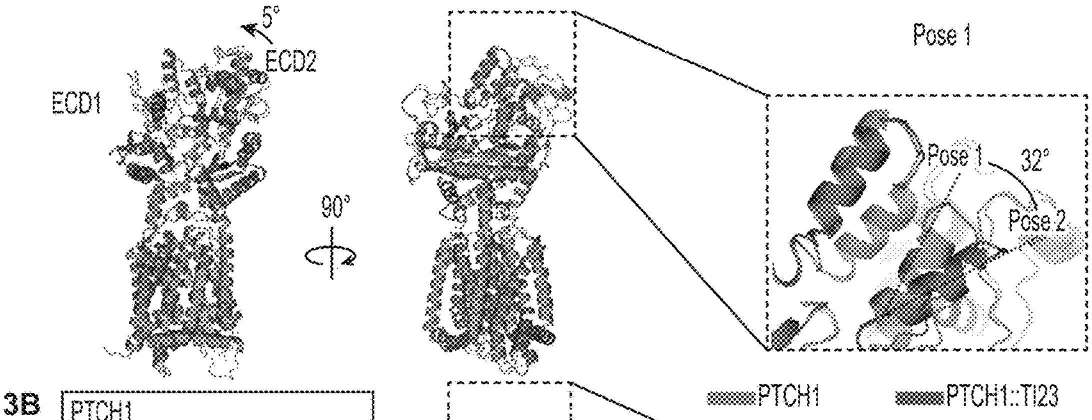
FIG. 3B
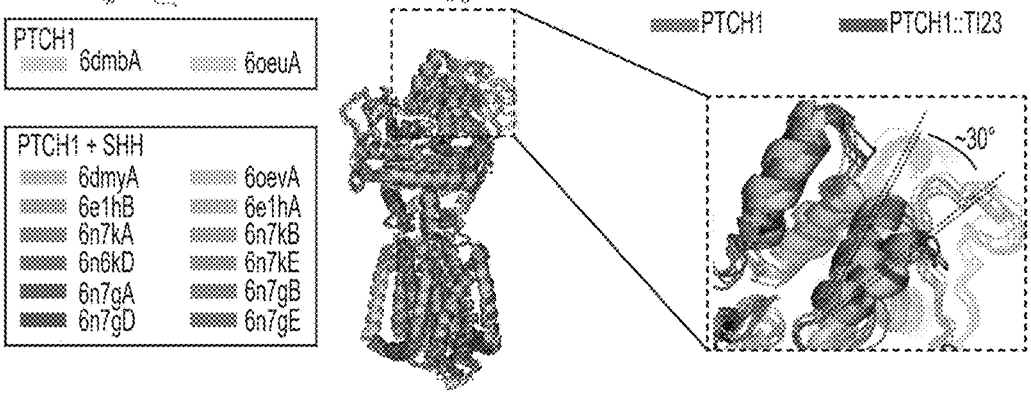
FIG. 3C
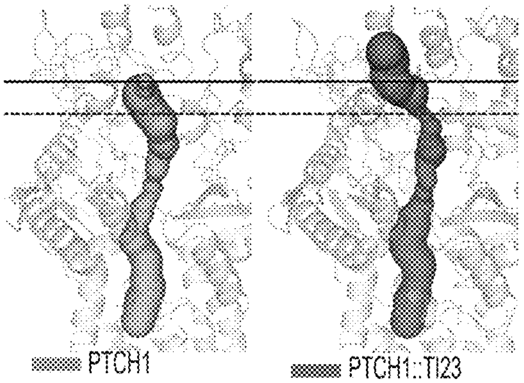
FIG. 3D
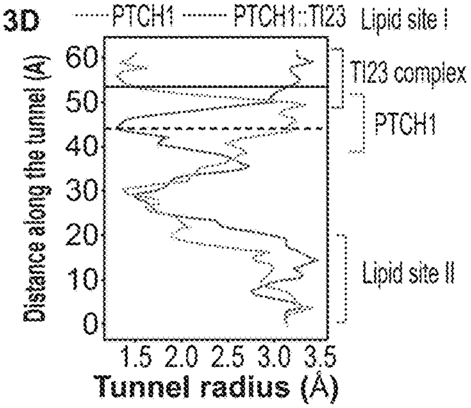
FIG. 3E
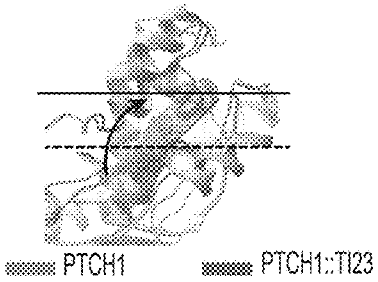
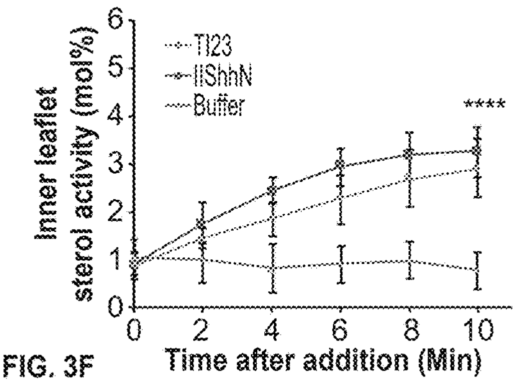
FIG. 3F FIG. 5G
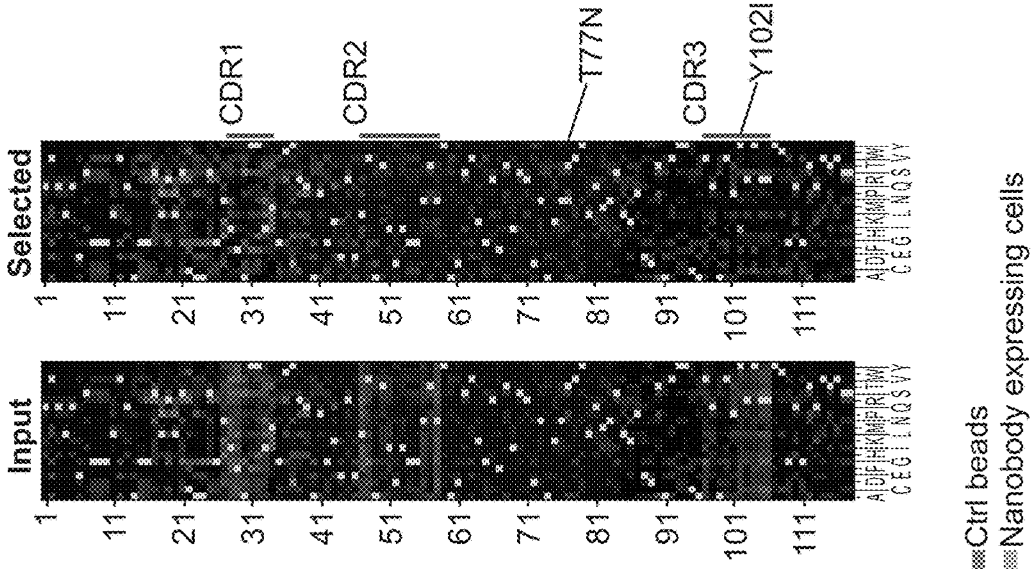
FIG. 5E
FIG. 5F
FIG. 5H
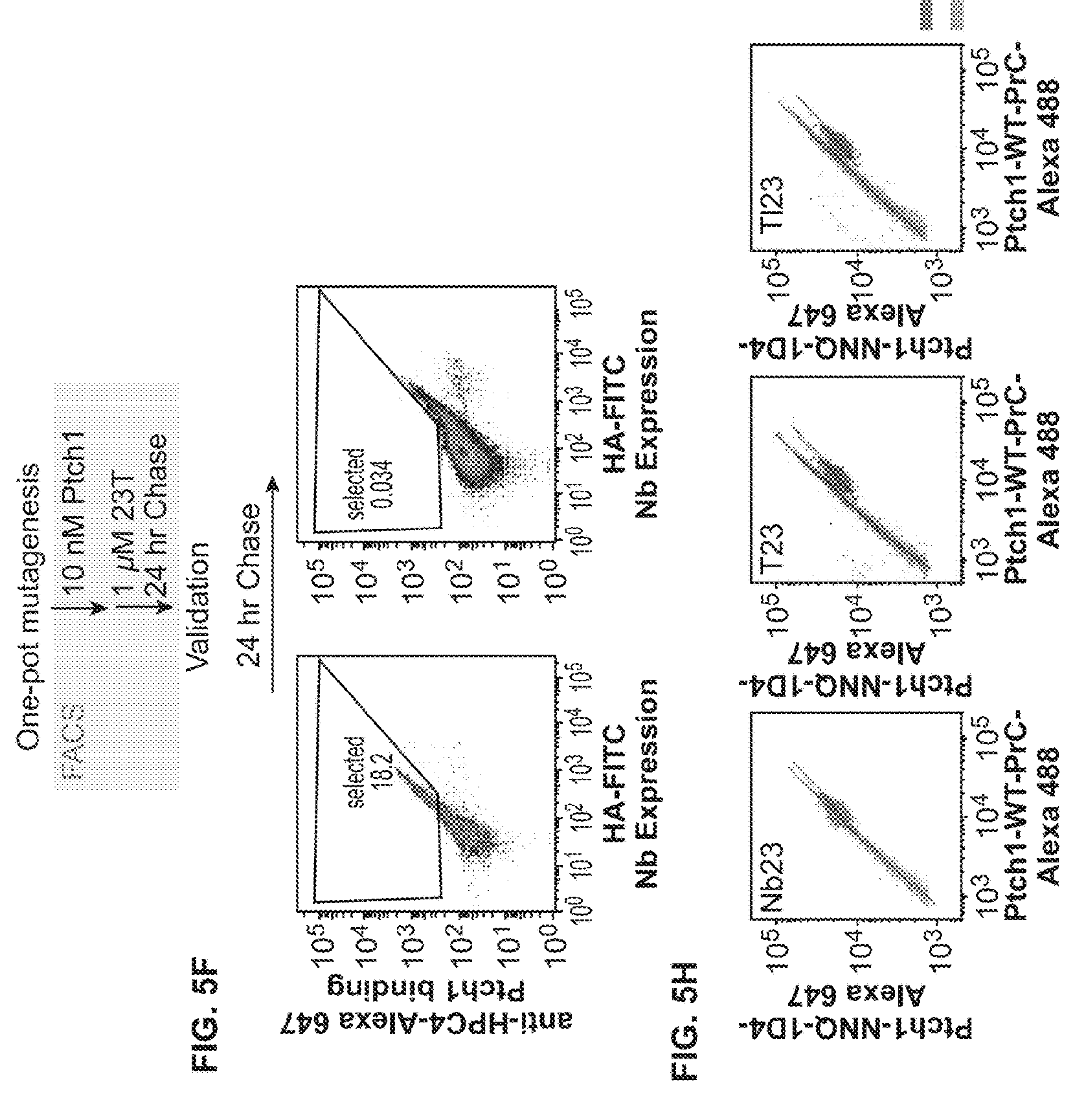

FIG. 6A
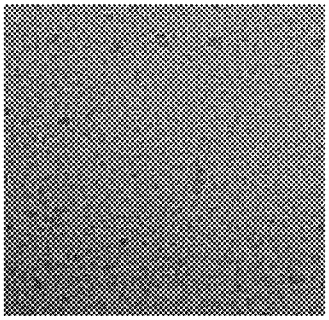
FIG. 6B
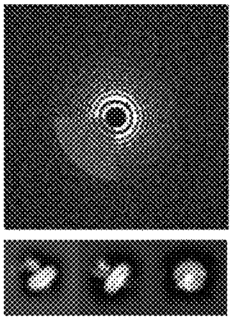
FIG. 6C
FIG. 6D
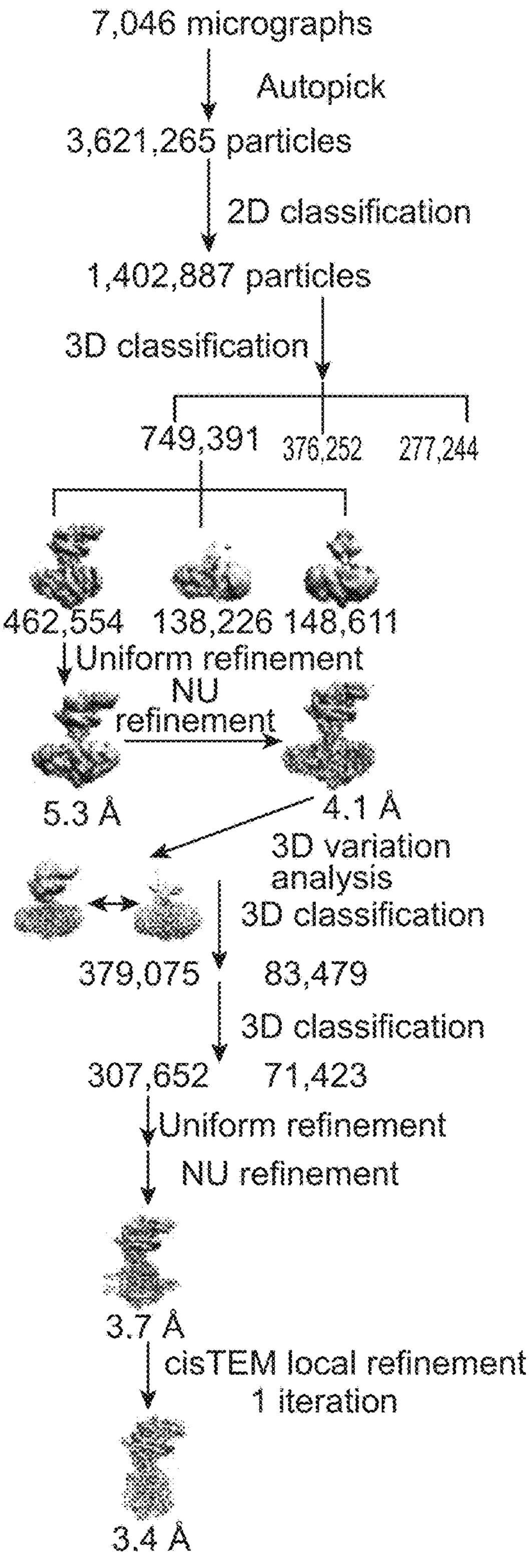

POTENT ANTIGEN-BINDING DOMAINS THAT BIND PATCHED1 FOR ACTIVATION OF THE HEDGEHOG SIGNALING PATHWAY

CROSS REFERENCE TO RELATED APPLICATION

This application is a U.S. National Stage Application of PCT Application No. PCT/US2021/052192, filed Sep. 27, 2021. Which Application claims priority to the filing date of U.S. Provisional Patent Application No. 63/083,544, filed Sep. 25, 2020, the disclosure of which is herein incorporated by reference.

STATEMENT REGARDING FEDERALLY SPONSORED RESEARCH

This invention was made with Government support under contract GM102498 awarded by the National Institutes of Health. The Government has certain rights in the invention.

INCORPORATION BY REFERENCE OF SEQUENCE LISTING PROVIDED AS A TEXT FILE

A Sequence Listing is provided herewith in a text file, (115487411_STAN-1688_SEQ_LIST_ST25.txt), created on May 22, 2026, and having a size of 40664 bytes. The contents of the text file are incorporated herein by reference in its entirety.

BACKGROUND

Hedgehog signaling functions in embryonic tissue patterning and in post-embryonic regulation of tissue homeostasis and regeneration. The postembryonic regenerative activities of the Hedgehog pathway clearly suggest potential therapeutic benefits of pathway activation. The only modality of pathway modulation tested clinically, however, is inhibition, with clear benefits for patients suffering from malignancies whose initiation and growth depend on pathway-activating mutations in the primary cells of the tumor, such as medulloblastoma and basal cell carcinoma.

A lack of clinical interest in pathway-activating therapies, despite availability of potent small molecule pathway activators, may be due to the expectation that such systemic treatments may cause overgrowth of mesenchyme and potential initiation or exacerbation of fibrosis in multiple organs. These dangerous side effects might be avoided by restricting pathway activation to specific cell types.

A pathway agonist conjugated to targeting agents would fulfill this purpose, but the native Hedgehog protein is difficult to engineer for cell type specificity. Mature Hedgehog protein contains two lipid modifications, including a cholesteryl moiety on its carboxy-terminus, and a palmitoyl adduct on its amino-terminus, which is especially critical for signaling activity. The requirement for lipid modification in signaling poses a challenge for large-scale production, storage, and further derivatization for tissue targeting. Other synthetic or genetically-encoded peptides that could easily be conjugated to targeting agents are currently lacking.

SUMMARY

Compositions and methods are provided relating to antigen binding domains (ABD) that preferentially bind and stabilize a specific human PTCH1 conformation, which activates the Hedgehog signaling pathway. The ABD are comprised of one or more variable region polypeptides that specifically bind to and stabilize PTCH1. In one embodiment, the ABD is provided as a nanobody, including without limitation the polypeptide of SEQ ID NO:24, e.g. SEQ ID NO: 18-SEQ ID NO:23. The nanobody of SEQ ID NO:23 is of particular interest. In other embodiments the sequence comprises a polypeptide set forth in any of SEQ ID NO:1-17.

The ABD may be linked, e.g. conjugated or fused, to various effector polypeptides, which include without limitation nanobodies; antibodies; and fragments and derivatives thereof. Embodiments include polynucleotides encoding the ABD; vectors comprising polynucleotides encoding the ABD; cells engineered to express the ABD; and pharmaceutical formulations comprising cells engineered to express the ABD. The ABD can be engineered for targeting by fusion to an antibody or other agent with tissue or cell-type specificity.

In some embodiments the ABD is provided as a polypeptide linked, e.g. conjugated or fused, to an immunoglobulin effector sequence, for example as an scFv, comprising an Fc sequence, e.g. a human immunoglobulin constant region of any isotype, e.g. IgG1, IgG2, IgG3, IgG4, IgA, etc., or a single variable region domain, e.g. a nanobody, etc.

In some embodiments a nanobody provided herein is, e.g. conjugated or fused, to a targeting moiety. A targeting moiety can be joined to a nanobody through a linker sequence, e.g. a polypeptide linker sequence. The moiety targets the nanobody to specific organs, tissues, tissue compartments, and cell types of interest.

In some embodiments a targeting moiety comprises a collagen-binding peptide. Many collagen-binding sequences are known in the art and find use for this purpose. In some embodiments the collagen is collagen I. In some embodiments the targeting moiety comprises SEQ ID NO:25. This sequence is shown to localize the nanobody to mesenchymal tissues.

In some embodiments a targeting moiety comprises a cytoplasmic tail that anchors a nanobody to the membrane of the primary cilium, which targeting moiety can be joined to a transmembrane domain. As the cilium is the major site of locatlization and Patched action in suppressing Smoothened, this targeting makes the nanobody a particularly potent activator of the Hh pathway. Membrane tethering furthermore restricts its action to the cell in which it is expressed (instead of being generally diffusible). This permits pathway activation restricted to any cell type that can be specifically targeted for expression of the nanobody, e.g. with a virus with a tropism to a specific cell type, or by expression under control of a cell type-specific promoter.

In some embodiments, the ABD comprises an amino acid sequence variant of one or more of the CDRs of the provided sequences, i.e. SEQ ID NO:1-23, and including without limitation SEQ ID NO:10 and variants thereof, i.e. SEQ ID NO:18-23. Variants may comprise one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally have a binding affinity or higher affinity; and epitope specificity as that of SEQ ID NO:23. In particular, residues noted in SEQ ID NO:24 for variation have been shown to be useful for increasing affinity of the ABD.

In some embodiments, a therapeutic method is provided. Pathway activation confers therapeutic benefits in regeneration of taste receptor cells of the tongue, which are often lost or diminished in chemotherapy patients, in protection or recovery from diseases such as colitis, reduction of tissue overgrowth in prostatic hypertrophy, acceleration of bone healing in diabetes, etc. A method can comprise introducing into a recipient in need an ABD polypeptide disclosed herein, e.g. a nanobody comprising SEQ ID NO:23.

In some embodiments, a vector comprising a polynucleotide sequence encoding a polypeptide comprising an ABD disclosed herein is provided, e.g. encoding a nanobody comprising SEQ ID NO:23, where the coding sequence is operably linked to a promoter active in the desired cell. In some embodiments, the promoter may be constitutive or inducible. Various vectors are known in the art and can be used for this purpose, e.g. viral vectors, plasmid vectors, minicircle vectors, which vectors can be integrated into the target cell genome, or can be episomally maintained. The vector and/or the polypeptide may be provided in a kit.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1H. Selection of conformation-selective nanobodies. (FIG. 1A) Alignment of transmembrane 4 (from top to bottom SEQ ID NOs: 31-34) and 10 (from top to bottom SEQ ID NOs: 35-38) from different RND transporters. The charged residues are marked by asterisks. (FIG. 1B) Flow chart of the steps for nanobody selection. The yeast library was first enriched with MACS for clones that bind to PTCH1-NNQ variant and then the population that prefers the NNQ variant was selected in FACS using PTCH1-NNQ and PTCH1-WT with different fluorescent labels. (FIG. 1C) Yeast cells stained with PTCH1-NNQ (FITC label) and PTCH1-WT (Alexa 647 label) are shown in the FACS plot. In the lower right quadrant are the cells that prefer NNQ variant to the WT variant. Due to more non-specific binding to Alexa 647 fluorophore than the FITC fluorophore, the double positive population shifts towards the upper left quadrant. (FIG. 1D) Nanobodies expressed and purified in *E. coli* were tested on Hedgehog-responsive 3T3 cells with a Gli-dependent luciferase reporter. GDC-0449, a pathway antagonist, is a control showing that nanobodies 17, 20 and 23 display weak activation in this assay. (FIG. 1E) Initial nanobody sequences of clones 17, 20 and 23 were mutagenized and selected in yeast display to obtain higher affinity clones (affinity maturation). After two rounds of affinity maturation, the new nanobody variant, named TI23, exhibits an EC50 of 8.6 nM in 3T3 cells, close to that of the native Hedgehog ligand. (FIG. 1F) The TI23 clone resulting from two rounds of affinity maturation showed a preference for binding to PTCH1-NNQ variant. Yeast cells expressing Nb23, T23 or TI23 were incubated with a mixture of 1:1 Protein C tagged PTCH1-WT and 1D4 tagged PTCH1-NNQ proteins, and then stained with antibodies against protein C tag or 1D4 tag. OneComp beads were used as a control for non-selective binding, as these beads bind to the constant region of kappa chain, and do not discriminate between different antibodies used for staining. (FIG. 1G) In the human mesenchymal cell line HEPM, TI23 activated Hedgehog response and induced transcription of pathway targets, GLI1 ($EC_{50}$=16.0 nM) and PTCH1 ($EC_{50}$=18.5 nM), as assayed by qPCR. (FIG. 1H) In NIH-3T3 cells, ShhNp and TI23 are titrated in a Gli-luciferase assay. $EC_{50}$ for ShhNp and TI23 are determined to be 1.4 nM and 6.9 nM, respectively. Error bars represent standard deviation and all data points represent the mean of a triplicate.

(FIG. 2A) The cryo-EM map of PTCH1::TI23 complex shows clear features of the proteins. PTCH1, TI23, (FIG. 2B) Protein model of the complex with PTCH1 and TI23. Lipid-like densities found in the map were modeled in sites I through IV. (FIG. 2C) Schematic view of PTCH1 showing the secondary structure elements and the relative positions of TI23 and the lipid-like densities. The key helix involved in the conformational change is highlighted as 'switch helix ". (FIG. 2D) The binding site of TI23 on PTCH1 overlaps with that of SHH (teal). The switch helix, is sandwiched by CDR1 and CDR3 of TI23. (FIG. 2E, FIG. 2F) The interactions between TI23 CDRs and PTCH1 are shown in detail. The hydrophobic interactions from CDR1 are viewed from above the membrane in e, whereas the hydrogen bond interactions from CDR3 are viewed from the ECD2 side of PTCH1 protein as in F.

FIG. 3A-3F. Conformational change induced by TI23. (FIG. 3A) Overlay of the structures of murine PTCH1 alone (PDB ID: 6mg8) or in complex with TI23 shows two major changes in the extracellular domain. The extracellular domain 2 between TM7 and TM8 turns around 5° pivoting on its connection to the transmembrane domain. A short helix (the switch helix) in extracellular domain 1 rotates ~32° towards the membrane. The conformation in PTCH1 alone and in the complex is referred to as pose 1 and 2, respectively. (FIG. 3B) Other published PTCH1 structures also fall into Pose 1 and 2 categories. In this overlay of other PTCH1 structures, pose 1-like structures are shown in shades of red, and pose 2-like structures in shades of blue. (FIG. 3C) The rotation of the switch helix alters the shape of the cavity within the extracellular domain. In the PTCH1 structure the conduit is capped at the end, as indicated by the dotted line ( . . . ) . . . . whereas in the TI23 structure, the end of the conduit is wide open to the exterior and the lower part is throttled, as marked by the dashed line (---). (FIG. 3D) The radii at different points along the conduit are plotted here, with the altered parts marked with two vertical lines. TI23 binding opens the upper end of the conduit but closes the lower part of lipid site I. (FIG. 3E) Position of the lipid-like density in site I changes with TI23 binding. The rotation of the switch helix may push the bound substrate outwards while closing down the entry route. (FIG. 3F) In Ptch1-MEFs transfected with PTCH1, plasma membrane inner leaflet (IPM) cholesterol activity increased immediately after adding purified TI23, or Hedgehog ligand (ShhN). Hedgehog ligand caused a slightly faster increase in IPM cholesterol activity, which plateaued after ~6 min. This may reflect the difference in efficacy of these two ligands, as TI23 induces ~75% maximum pathway activity at saturating concentration in Gli-dependent luciferase assays. In the control conditions, cholesterol activity did not change over the period of the assay. At the end point (t=10), cholesterol activity in TI23 or ShhN group is significantly higher than buffer treated group (ANOVA correction for multiple comparison, $p<0.0001$). Error bars represent standard deviation. For ShhN or TI23, n=10. For buffer only control, n=5.

(FIG. 4A) Mice were injected with AAV-DJ or treated with small molecule SAG21k for 2 weeks before collecting skin for histology analysis. Gli1 expression (relative to Hprt1) was activated in the dorsal skin of animals receiving TI23, ShhN or the small molecule SAG21k, suggesting that TI23 activated the Hedgehog pathway in the skin. Mean and standard error of the mean was plotted. (FIG. 4B) Histology of the dorsal skin suggests that hair follicles in the control group are in quiescent telogen phase, whereas hair follicles grow and invade the adipocyte layer in with TI23, ShhN, or SAG21k treatment, indicating induction of anagen. (FIG. 4C) Hair regrowth observed two weeks after virus injection is much accelerated in TI23 or ShhN-treated animals as compared to the control group, suggesting that these hair follicles are in active anagen phase.

FIG. 5A-5H. Selection of nanobody. (FIG. 5A) Yeast cells expressing the initial clones were stained with the antibody used during FACS to ensure that the nanobody binds directly to PTCH1 protein. As summarized in FIG. 5B, Clones 4, 9 and 15 showed strong binding to the antibody and are thus false-positive clones during the selection. All the other clones were then purified and tested for activity on cells except for clone 13, which could not be expressed or purified from bacteria. (FIG. 5C) Flow chart of the first round of affinity maturation. Nanobody sequences from clone 17, 20 and 23 were mutagenized with error-prone PCR and transformed into yeast. After enriching for PTCH1 binding clones with MACS, the yeast cells are selected in FACS. In the final FACS steps, the cells were first incubated with PTCH1 to allow the nanobodies to bind and after wash, the cells were incubated with the parent nanobody proteins, to compete PTCH1 off the cell surface. FACS plots before and after the competitive chase are shown in FIG. 5D. The cells that retain binding to PTCH1 were selected by FACS. (FIG. 5E) Flow chart of the second round of affinity maturation. The sequence was mutagenized with one-pot mutagenesis and transformed into yeast. Yeast cells expressing the nanobody were selected in FACS with a similar competitive chase. The FACS plots before and after the competition were shown in FIG. 5F. (FIG. 5G) The amino acid sequences of the round 2 affinity maturation library were determined with MiSeq and are plotted here. The selection enriched for T77N and Y1021 variants. (FIG. 5H) Yeast cells expressing Nb23, T23, or TI23 preferentially bind to PTCH1-WT over PTCH1-NNQ. OneComp beads that bind to all antibodies equally well were used as a control.

FIG. 6A-6G. Cryo-EM data validation. (FIG. 6A) Protein particles are clearly visible in raw cryo-EM micrographs. (FIG. 6B) The parameters for contrast transfer function (CTF) are well fitted for this dataset. (FIG. 6C) 2D classification revealed clear views of PTCH1-TI23 complex. (FIG. 6D) Cryo-EM data processing was summarized in the flow chart here. All steps were carried out in cryoSPARC, except for the last local refinement step, which was performed with cisTEM. (FIG. 6E) The orientation of the particles is summarized in the spherical histogram here. Most particles are oriented along the equator of the protein. (FIG. 6F) The FSC curves of the final refinement were plotted here. The resolution of the final map is estimated to be 3.4 Å according to the 0.143 gold standard FSC. (FIG. 6G) Local resolution of the final reconstruction was estimated in cryoSPARC and shown in the 3D models here. Most regions were well resolved except for part of the nanobody.

(FIG. 7A) The protein model fits the cryo-EM well. The high quality map enables confident modeling of not only alpha helical structures but also beta strands in the extracellular domain. Presence of clear side chain densities in the key transmembrane helices 4 and 10 enables modeling of the interaction of the key charged triad. (FIG. 7B) A large density present in the extracellular domain fits well with GDN and is thus likely to be a bound GDN molecule. (FIG. 7C) The model fits well with the cryo-EM map, as indicated by the model-map FSC curves. (FIG. 7D) The interactions between TM4 and TM10 are distinct between the TI23 bound murine PTCH1 structure (left) and the SHH-bound human PTCH1 structure (right; H1099, E1095, and D513 correspond to murine residues H1085, E1081, and D499).

(FIG. 8B) A single site distal to the membrane alters conformation in known PTCH1 structures. PTCH1: TI23 and PTCH1 alone (6mg8) are shown here as examples.

FIG. 9B: Diagram of dorsal tongue with epithelium and mesenchyme compartment indicated. FIG. 9C & FIG. 9D: qPCR result of relative expression of Gli1 normalized to Hprt housekeeping gene. AAV was packaged in AAV-DJ and delivered to 7-8 week old FVB mice by retroorbital injection. Note that TI23 without Collagen1 targeting sequence was injected at 11.7× and 13.5× higher titer than Ti23Col1 and NB4. Virus titer is indicated as viral genomes (vg) injected per mouse: 7.1e+010 vg/mouse for NB4Collagen1 (negative control), 8.2e+010 vg/mouse for TI23Collagen1, 9.57e+011 vg/mouse for TI23.

DETAILED DESCRIPTION

Definitions

Figure 1F:
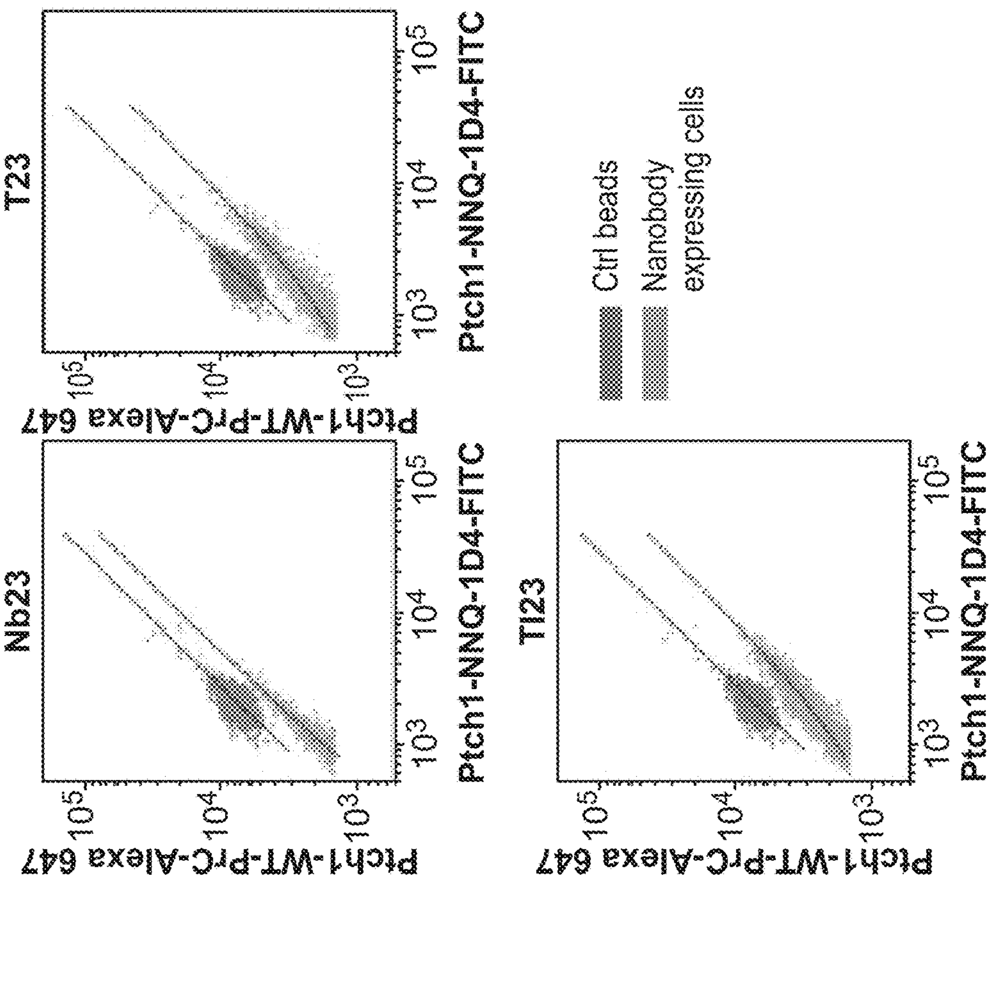

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

As used herein, a "nanobody" refers to a single-domain antibody, which may be designated sdAb, which is an antibody fragment consisting of a single monomeric variable antibody domain that is able to bind selectively to an antigen. A nanobody may comprise heavy chain variable domains or light chain variable domains. Specifically, a nanobody of the disclosure comprises heavy chain variable domain. A nanobody may be derived from camelids ($V_HH$ fragments) or cartilaginous fishes ($V_{NAR}$ fragments). Alternatively, a nanobody may be derived from splitting the dimeric variable domains from IgG into monomers.

A nanobody comprises a variable region primarily responsible for antigen recognition and binding and a framework region. The "variable region," also called the "complementarity determining region" (CDR), comprises loops which differ extensively in size and sequence based on antigen recognition. CDRs are generally responsible for the binding specificity of the nanobody. Distinct from the CDRs is the framework region. The framework region is relatively conserved and assists in overall protein structure. The framework region may comprise a large solvent-exposed surface consisting of a β-sheet and loop structure. A signal sequence, as known in the art, can be included, which is then cleaved from the mature nanobody.

The present disclosure provides for nanobodies that bind to patched and activate the hedgehog signaling pathway. The nanobodies comprise an single variable region antigen binding domain (ABD). As used herein, the term ABD refers to the variable region polypeptide that specifically binds to the desired antigen. An ABD is the minimum fragment that contains a complete antigen-recognition and binding site, in the present invention as a single polypeptide. It is in this configuration that the CDRS of the variable domain define an antigen-binding site on the surface of the domain. Examples of nanobodies include those set forth herein, including without limitation SEQ ID NO:10; and SEQ ID NO:18-23, particularly SEQ ID NO:23.

Determination of affinity for the antigen can be performed using methods known in the art, e.g. Biacore measurements, etc. Members of the nanobody family may have an affinity for the cognate antigen with a Kd of from about $10^{-7}$ to around about $10^{-11}$, including without limitation: from about $10^{-7}$ to around about $10^{-10}$; from about $10^{-7}$ to around about $10^{-9}$; from about $10^{-7}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for activity in, for example, and in vitro or pre-clinical model, and assessment of potential toxicity.

A nanobody or ABD "which binds" an antigen of interest, is one that binds the antigen with sufficient affinity such that the nanobody or binding molecule is useful as a diagnostic and/or therapeutic agent in targeting the antigen, and does not significantly cross-react with other proteins. In such embodiments, the extent of binding of the nanobody or other binding molecule to a non-targeted antigen will usually be no more than 10% as determined by fluorescence activated cell sorting (FACS) analysis or radioimmunoprecipitation (RIA).

A "functional" or "biologically active" nanobody or antigen-binding molecule is one capable of exerting one or more of its natural activities in structural, regulatory, biochemical or biophysical events. For example, a functional nanobody or other binding molecule may have the ability to specifically bind an antigen and the binding may in turn elicit or alter a cellular or molecular event such as signaling transduction or enzymatic activity.

The term "variable" refers to the fact that certain portions of the variable domains differ extensively in sequence and are used in the binding and specificity of each particular variable domain for its particular antigen. However, the variability is not evenly distributed throughout the variable domains. It is concentrated in hypervariable regions. The more highly conserved portions of variable domains are called the framework regions (FRs).

The term "hypervariable region" when used herein refers to the amino acid residues responsible for antigen-binding. The hypervariable region may comprise amino acid residues from a "complementarity determining region" or "CDR", and/or those residues from a "hypervariable loop". "Framework Region" or "FR" residues are those variable domain residues other than the hypervariable region residues as herein defined.

The term "antibody" herein is used in the broadest sense and specifically covers monoclonal antibodies, polyclonal antibodies, monomers, dimers, multimers, multispecific antibodies (e.g., bispecific antibodies), heavy chain only antibodies, three chain antibodies, single chain Fv, nanobodies, etc., and also include antibody fragments, so long as they exhibit the desired biological activity (Miller et al (2003) Jour. of Immunology 170:4854-4861). Antibodies may be murine, human, humanized, chimeric, or derived from other species. The term antibody may reference a full-length heavy chain, a full length light chain, an intact immunoglobulin molecule; or an immunologically active portion of any of these polypeptides, i.e., a polypeptide that comprises an antigen binding site that immunospecifically binds an antigen of a target of interest or part thereof. The immunoglobulin can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. The immunoglobulins can be derived from any species. In one aspect, the immunoglobulin is of largely human origin.

Unless specifically indicated to the contrary, the term "conjugate" as described and claimed herein is defined as a heterogeneous molecule formed by the covalent attachment of one or more nanobody fragment(s) to one or more additional molecules, such as polymer molecule(s), labels, cytotoxic agents, targeting moieties, etc. For example a polymer may be water soluble, i.e. soluble in physiological fluids such as blood, and wherein the heterogeneous molecule is free of any structured aggregate. A conjugate of interest is PEG. The word "label" when used herein refers to a detectable compound or composition which is conjugated directly or indirectly to the nanobody. The label may itself be detectable by itself (e.g., radioisotope labels or fluorescent labels) or, in the case of an enzymatic label, may catalyze chemical alteration of a substrate compound or composition which is detectable.

Linker. The domains of a protein may be separated by a linker, e.g. a polypeptide linker, or a non-peptidic linker, etc. In some embodiments the linker is a rigid linker, in other embodiments the linker is a flexible linker. In some embodiments, the linker moiety is a peptide linker. In some embodiments, the peptide linker comprises 2 to 100 amino acids. In some embodiments, the peptide linker comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 but no greater than 100 amino acids. In some embodiments, the peptide linker is between 5 to 75, 5 to 50, 5 to 25, 5 to 20, 5 to 15, 5 to 10 or 5 to 9 amino acids in length. Exemplary linkers include linear peptides having at least two amino acid residues such as Gly-Gly, Gly-Ala-Gly, Gly-Pro-Ala, Gly-Gly-Gly-Gly-Ser (SEQ ID NO:39). Suitable linear peptides include poly glycine, polyserine, polyproline, polyalanine and oligopeptides consisting of alanyl and/or serinyl and/or prolinyl and/or glycyl amino acid residues. In some embodiments, the peptide linker comprises the amino acid sequence selected from the group consisting of $Gly_9$ (SEQ ID NO:40), $Glu_9$ (SEQ ID NO: 41), $Ser_9$ (SEQ ID NO:42), $Gly_5$-Cys-$Pro_2$-Cys (SEQ ID NO:43), $(Gly_4\text{-}Ser)_3$ (SEQ ID NO: 44), Ser-Cys-Val-Pro-Leu-Met-Arg-Cys-Gly-Gly-Cys-Cys-Asn (SEQ ID NO:45), Pro-Ser-Cys-Val-Pro-Leu-Met-Arg-Cys-Gly-Gly-Cys-Cys-Asn (SEQ ID NO:46), Gly-Asp-Leu-Ile-Tyr-Arg-Asn-Gln-Lys (SEQ ID NO: 47), and Gly9-Pro-Ser-Cys-Val-Pro-Leu-Met-Arg-Cys-Gly-Gly-Cys-Cys-Asn (SEQ ID NO:48). In one embodiment a linker comprises the amino acid sequence GSTSGSGKSSEGKG (SEQ ID NO:49), or (GGGGS) n (SEQ ID NO:39), where n is 1, 2, 3, 4, 5, etc.; however many such linkers are known and used in the art and may serve this purpose.

Chemical groups that find use in linking binding domains include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; lipids, and the like, as known in the art.

Transmembrane domain. Proteins of the disclosure may comprise a transmembrane domain joining the surface domain with an intracellular cytoplasmic domain. The transmembrane domain is comprised of any polypeptide sequence which is thermodynamically stable in a eukaryotic cell membrane. The transmembrane spanning domain may be derived from the transmembrane domain of a naturally occurring membrane spanning protein or may be synthetic. In designing synthetic transmembrane domains, amino acids favoring alpha-helical structures are preferred. Transmembrane domains may be comprised of approximately 10, 11, 12, 13, 14, 15, 16, 17, 18, 19, 20, 21, 22, 22, 23, 24 or more amino acids favoring the formation having an alpha-helical secondary structure. Amino acids that favor alpha-helical conformations are well known in the art. See, e.g Pace, et al. (1998) Biophysical Journal 75:422-427. Amino acids that are particularly favored in alpha helical conformations include methionine, alanine, leucine, glutamate, and lysine. In some embodiments, the transmembrane domain may be derived from the transmembrane domain from type I membrane spanning proteins, such as CD3ζ, CD4, CD8, CD28, etc., including without limitation SEQ ID NO:28.

A "targeting moiety" as used herein is any moiety that is able to bind to, i.e., a "binding partner of," an intended target of the therapy, to localize to a cell or tissue of interest, etc.

For instance, a targeting moiety may be a receptor ligand in instances when the target is a cellular receptor. In some embodiments a targeting moiety is an antigen binding domain, in other embodiments a shorter polypeptide sequence is preferred; other examples of targeting moieties are known in the art and may be used, such as aptamers, avimers, receptor-binding ligands, nucleic acids, biotin-avidin binding pairs, binding peptides or proteins, etc. In some embodiments a targeting moiety is joined to a nanobody disclosed herein through a linker peptide.

A targeting moiety can be a peptide that binds to a cell surface molecules of interest, including, without limitation, a collagen binding peptide; an integrin binding peptide having an RGD motif; a cilia localization sequence (SEQ ID NO:29), and the like. Collagen binding peptides include, for example, (SEQ ID NO:26), a fibronectin collagen binding sequence such as CQDSETRTFY (SEQ ID NO:30); or others known in the art, for example see Farndale (2019) Essays Biochem 63 (3): 337-348, herein specifically incorporated by reference. In some embodiments the targeting moiety is itself a nanobody or single-chain antibody that binds to a desired cell type or extracellular compartment.

"Homology" between two sequences is determined by sequence identity. If two sequences, which are to be compared with each other, differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

"Variant" refers to polypeptides having amino acid sequences that differ to some extent from a native sequence polypeptide. Ordinarily, amino acid sequence variants will possess at least about 80% sequence identity, more preferably, at least about 90%, at least 95%, at least 99% homologous by sequence, for example having 1, 2, 3, 4, or more amino acid substitutions, additions or deletions at certain positions within the reference amino acid sequence.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operably linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Binding affinity" generally refers to the strength of the sum total of noncovalent interactions between a single binding site of a molecule (e.g., an nanobody or other binding molecule) and its binding partner (e.g., an antigen or receptor). The affinity of a molecule X for its partner Y can generally be represented by the dissociation constant (Kd). Affinity can be measured by common methods known in the art, including those described herein. Low-affinity antibodies bind antigen (or receptor) weakly and tend to dissociate readily, whereas high-affinity antibodies bind antigen (or receptor) more tightly and remain bound longer.

In an embodiment, affinity is determined by surface plasmon resonance (SPR), e.g. as used by Biacore systems. The affinity of one molecule for another molecule is determined by measuring the binding kinetics of the interaction, e.g. at 25° C.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; avians, and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

Methods of Use

The nanobodies are useful for both prophylactic and therapeutic purposes. Thus, as used herein, the term "treating" is used to refer to both prevention of disease, and treatment of a pre-existing condition. In certain instances, prevention indicates inhibiting or delaying the onset of a disease or condition, in a patient identified as being at risk of developing the disease or condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests. Patients for treatment may be mammals, e.g. primates, including humans, may be laboratory animals, e.g. rabbits, rats, mice, etc., particularly for evaluation of therapies, horses, dogs, cats, farm animals, etc.

The dosage of the therapeutic formulation, e.g., pharmaceutical composition, will vary widely, depending upon the nature of the condition, the frequency of administration, the manner of administration, the clearance of the agent from the host, and the like. In particular embodiments, the initial dose can be larger, followed by smaller maintenance doses. In certain embodiments, the dose can be administered as infrequently as weekly or biweekly, or more often fractionated into smaller doses and administered daily, semi-weekly, or otherwise as needed to maintain an effective dosage level.

In some embodiments of the invention, administration of the composition or formulation comprising a nanobody is performed by local administration. Local administration, as used herein, may refer to topical administration, but also refers to injection or other introduction into the body at a site of treatment. Examples of such administration include intramuscular injection, subcutaneous injection, intraperitoneal injection, and the like. In other embodiments, the composition or formulation comprising a nanobody is administered systemically, e.g., orally or intravenously. In one embodiment, the composition of formulation comprising a nanobody is administered by infusion, e.g., continuous infusion over a period of time, e.g., 10 min, 20 min, 3 min, one hour, two hours, three hours, four hours, or greater. For regeneration of taste receptor cells there can be, in addition, topical application to the tongue, e.g. mouthwash, incorporation into a film to be placed on the tongue, and the like. For treatment of colitis there can be, for example, a suppository method. For prostatic overgrowth there can be, for example, transurethral delivery; injection into prostate tissue; etc.

In some embodiments of the invention, the compositions or formulations are administered on a short term basis, for example a single administration, or a series of administrations performed over, e.g. 1, 2, 3 or more days, up to 1 or 2 weeks, in order to obtain a rapid, significant increase in activity. The size of the dose administered must be determined by a physician and will depend on a number of factors, such as the nature and gravity of the disease, the age and state of health of the patient and the patient's tolerance to the drug itself.

In certain methods of the present invention, an effective amount of a composition comprising a nanobody is provided to cells, e.g. by contacting the cell with an effective amount of that composition to achieve a desired effect. In particular embodiments, the contacting occurs in vitro, ex vivo or in vivo. In particular embodiments, the cells are derived from or present within a subject in need of increased Hedgehog signaling.

In other embodiments a nucleic acid composition encoding a nanobody disclosed herein is provided to a cell, e.g. using a viral vector, plasmid vector, CRISPR targeting, and the like to express the polynucleotide in a desired cell.

In some methods of the invention, an effective amount of the subject composition is provided to enhance Hedgehog signaling in a cell. Biochemically speaking, an effective amount or effective dose of a nanobody is an amount to increase Hedgehog signaling in a cell by at least 30%, at least 40%, at least 50%, at least 60%, at least 70%, at least 80%, at least 90%, at least 95%, or by 100% relative to the signaling in the absence of the nanobody. The amount of modulation of a cell's activity can be determined by a number of ways known to one of ordinary skill in the art.

In a clinical sense, an effective dose of a nanobody composition is the dose that, when administered to a subject for a suitable period of time, e.g., at least about one week, and maybe about two weeks, or more, up to a period of about 4 weeks, 8 weeks, or longer, will evidence an alteration in the symptoms associated with lack of signaling. In some embodiments, an effective dose may not only slow or halt the progression of the disease condition but may also induce the reversal of the condition. It will be understood by those of skill in the art that an initial dose may be administered for such periods of time, followed by maintenance doses, which, in some cases, will be at a reduced dosage.

The calculation of the effective amount or effective dose of nanobody composition to be administered is within the skill of one of ordinary skill in the art, and will be routine to those persons skilled in the art. Needless to say, the final amount to be administered will be dependent upon the route of administration and upon the nature of the disorder or condition that is to be treated.

Cells suitable for use in the subject methods are cells that comprise one or more Fzd receptors. The cells to be contacted may be in vitro, that is, in culture, or they may be in vivo, that is, in a subject. Cells may be from/in any organism, but are preferably from a mammal, including humans, domestic and farm animals, and zoo, laboratory or pet animals, such as dogs, cats, cattle, horses, sheep, pigs, goats, rabbits, rats, mice, frogs, zebrafish, fruit fly, worm, etc. Preferably, the mammal is human. Cells may be from any tissue. Cells may be frozen, or they may be fresh. They may be primary cells, or they may be cell lines. Often cells are primary cells used in vivo, or treated ex vivo prior to introduction into a recipient.

Cells in vitro may be contacted with a composition comprising a nanobody by any of a number of well-known methods in the art. For example, the composition may be provided to the cells in the media in which the subject cells are being cultured. Nucleic acids encoding the nanobody may be provided to the subject cells or to cells co-cultured with the subject cells on vectors under conditions that are well known in the art for promoting their uptake, for example electroporation, calcium chloride transfection, and lipofection. Alternatively, nucleic acids encoding the nanobody may be provided to the subject cells or to cells cocultured with the subject cells via a virus, i.e. the cells are contacted with viral particles comprising nucleic acids encoding the polypeptide. Retroviruses, for example, lentiviruses, are particularly suitable to the method of the invention, as they can be used to transfect non-dividing cells (see, for example, Uchida et al. (1998) P.N.A.S. 95 (20): 11939-44). Commonly used retroviral vectors are "defective", i.e. unable to produce viral proteins required for productive infection. Rather, replication of the vector requires growth in a packaging cell line.

The therapeutic dose may be at least about 1 μg/kg body weight, at least about 5 μg/kg body weight; at least about 10 μg/kg body weight, at least about 50 μg/kg body weight, at least about 100 μg/kg body weight, at least about 250 μg/kg body weight, at least about 500 μg/kg body weight, and not more than about 10 mg/kg body weight. It will be understood by one of skill in the art that such guidelines will be adjusted for the molecular weight of the active agent, e.g. in the use of protein conjugates, e.g. pegylated proteins. The dosage may also be varied for localized administration, e.g. intranasal, inhalation, etc., or for systemic administration, e.g. i.m., i.p., i.v., and the like.

Likewise, cells in vivo may be contacted with the subject nanobody compositions by any of a number of well-known methods in the art for the administration of peptides, small molecules, or nucleic acids to a subject. The nanobody composition can be incorporated into a variety of formulations or pharmaceutical compositions, which in some embodiments will be formulated in the absence of detergents, liposomes, etc., as would be required for the formulation of native Hedgehog proteins.

In some embodiments, the compounds of the invention are administered for use in treating diseased or damaged tissue, for use in tissue regeneration and for use in cell growth and proliferation, and/or for use in tissue engineering. In particular, the present invention provides a nanobody or nanobody encoding polynucleotide according to the invention for use in tissue regeneration or repair, or other pathological conditions.

Conditions of interest for treatment with the compositions of the invention include, without limitation, a number of conditions in which regenerative cell growth is desired. Such conditions can include, for example, enhanced bone growth or regeneration, e.g. on bone regeneration, bone grafts, healing of bone fractures, etc.; regeneration of taste receptors, treatment of colitis or mucositis, and the like.

Conditions in which enhanced bone growth is desired may include, without limitation, fractures, grafts, ingrowth around prosthetic devices, and the like. The nanobodies find use in enhancing bone healing. In many clinical situations, the bone healing condition are less ideal due to decreased activity of bone forming cells, e.g. within aged people, following injury, in osteogenesis imperfecta, etc. A variety of bone and cartilage disorders affect aged individuals. Such tissues are normally regenerated by mesenchymal stem cells. Included in such conditions is osteoarthritis. In methods of accelerating bone repair, a pharmaceutical composition of the present invention is administered to a patient suffering from damage to a bone, e.g. following an injury. The formulation is preferably administered at or near the site of injury, following damage requiring bone regeneration. In an alternative method, patient suffering from damage to a bone is provided with a composition comprising bone marrow cells, e.g. a composition including mesenchymal stem cells, bone marrow cells capable of differentiating into osteoblasts; etc. The bone marrow cells may be treated ex vivo with a pharmaceutical composition or proteins in a dose sufficient to enhance regeneration.

In other embodiments, the compositions of the invention are used in the regeneration of taste receptor tissue. Compositions of the present invention can be used, for example, in an infusion; in a matrix or other depot system; or other topical application to the tongue for enhancement of regeneration.

Various epidermal conditions benefit from treatment with the compounds of the invention, for example when there is a break-down of the rapidly divided epithelial cells lining the gastro-intestinal tract, leaving the tissue open to ulceration and infection, resulting, for example, in colitis, mucositis, etc. Mucosal tissue, also known as mucosa or the mucous membrane, lines all body passages that communicate with the air, such as the respiratory and alimentary tracts, and have cells and associated glands that secrete mucus. The part of this lining that covers the mouth, called the oral mucosa, is one of the most sensitive parts of the body and is particularly vulnerable to chemotherapy and radiation.

In some embodiments a therapeutic method is provided for treating hair loss, with pathway activation to encourage hair regrowth (see, for example, Paladini et al. J Invest Dermatol 125:638-646, 2005), in such embodiments delivery can be accomplished by, for example, transdermal patches or microneedle delivery.

For the treatment of non-invasive high risk bladder cancer, methods are known for instillation into the bladder of BCG (*Bacillus* Calmette-Guerin, bovine TB). In some embodiments, coding sequences for the subject ABDs are introduced into these bacteria for expression and secretion. Hh pathway activation suppresses progression of bladder cancer from non-invasive to its lethal invasive form (see, for example, Shin et al. Cancer Cell 14; Roberts et al. Cancer Cell 17).

The patient may be any animal (e.g., a mammal), including, but not limited to, humans, non-human primates, rodents, and the like. Typically, the patient is human. The methods of treatment and medical uses of the surrogates of the invention or compounds or compositions comprising surrogates of the invention promote tissue regeneration.

In some embodiments, the invention provides methods of treatment and medical uses, as described previously, wherein two or more nanobodies are administered to an animal or patient simultaneously, sequentially, or separately.

In some embodiments, the invention provides methods of treatment and medical uses, as described previously, wherein one or more nanobodies of the invention are administered to an animal or patient in combination with one or more further compound or drug, and wherein said nanobodies and said further compound or drug are administered simultaneously, sequentially, or separately.

The nanobodies of the invention also have widespread applications in non-therapeutic methods, for example in vitro research methods.

Expression construct: In the present methods, a nanobody may be produced by recombinant methods. Amino acid sequence variants of are prepared by introducing appropriate nucleotide changes into the DNA coding sequence. A signal sequence can be included for secretion of the nanobody. Such variants represent insertions, substitutions, and/or specified deletions of, residues within or at one or both of the ends of the amino acid sequence. Any combination of insertion, substitution, and/or specified deletion is made to arrive at the final construct, provided that the final construct possesses the desired biological activity as defined herein. The amino acid changes also may alter post-translational processes of the polypeptide, such as changing the number or position of glycosylation sites, altering the membrane anchoring characteristics, and/or altering the cellular location by inserting, deleting, or otherwise affecting the leader sequence of a polypeptide.

The nucleic acid encoding the nanobody can be inserted into a replicable vector for expression. Many such vectors are available. The vector components generally include, but are not limited to, one or more of the following: an origin of replication, one or more marker genes, an enhancer element, a promoter, and a transcription termination sequence.

Expression vectors will contain a promoter that is recognized by the host organism and is operably linked to the nanobody coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature.

Promoters suitable for use with prokaryotic hosts include the β-lactamase and lactose promoter systems, alkaline phosphatase, a tryptophan (trp) promoter system, and hybrid promoters such as the tac promoter. However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Promoter sequences are known for eukaryotes. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a Hindlll E restriction fragment.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, «-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs.

Construction of suitable vectors containing one or more of the above-listed components employs standard techniques. Isolated plasmids or DNA fragments can be cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting.

In addition to prokaryotes, eukaryotic microbes such as filamentous fungi or yeast are suitable expression hosts. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as *K. lactis, K. fragilis*, etc.; *Pichia pastoris; Candida; Neurospora crassa; Schwanniomyces* such as *Schwanniomyces occidentalis*; and filamentous fungi such as *Penicillium, Tolypocladium*, and *Aspergillus* hosts such as A. nidulan, and *A. niger.*

Plant cell cultures of cotton, corn, potato, soybean, *petunia*, tomato, and tobacco can be utilized as hosts. Typically, plant cells are transfected by incubation with certain strains of the bacterium *Agrobacterium tumefaciens*. During such incubation of the plant cell culture, the DNA coding sequence is transferred to the plant cell host such that it is transfected, and will, under appropriate conditions, express the DNA. In addition, regulatory and signal sequences compatible with plant cells are available, such as the nopaline synthase promoter and polyadenylation signal sequences.

Examples of useful mammalian host cell lines are mouse L cells (L-M [TK-], ATCC #CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transfected with the above-described expression vectors for nanobody production, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Hedgehog pathway activation through nanobody-mediated conformational blockade of the Patched sterol conduit Activation of the Hedgehog pathway has therapeutic value for improved bone healing, taste receptor cell regeneration, and alleviation of colitis or other conditions. Systemic pathway activation, however, can be detrimental and agents amenable to tissue targeting for therapeutic application have been lacking. We have developed a novel agonist, a conformation-specific nanobody against the Hedgehog receptor Patched1. This nanobody potently activates the Hedgehog pathway in vitro and in vivo by stabilizing an alternative conformation of a Patched1 "switch helix", as revealed in our cryo-EM structure. Nanobody-binding likely traps Patched in one stage of its transport cycle, thus preventing substrate movement through the Patched1 sterol conduit. Unlike native Hedgehog ligand, this nanobody does not require lipid modifications for its activity, facilitating mechanistic studies of Hedgehog pathway activation and the engineering of pathway activating agents for therapeutic use. Our conformation-selective nanobody approach is generally applicable to the study of other PTCH1 homologs.

The primary receptor for Hedgehog is Patched1 (PTCH1), which maintains pathway quiescence by suppressing Smoothened (SMO) a downstream G-protein coupled receptor (GPCR)-like protein. When bound to Hedgehog, PTCH1 is inactivated, permitting SMO to become active and trigger downstream signaling events. Mechanistically, the activation of SMO requires binding of a sterol, likely entering the 7TM bundle from the inner leaflet of the plasma membrane. PTCH1 is proposed to prevent SMO activation by transporting sterols from the inner leaflet of the plasma membrane, thereby limiting SMO access to activating sterols. A hydrophobic conduit coursing through the PTCH1 extracellular domain is required for this transport activity and Hedgehog blocks this conduit and inactivates PTCH1 by inserting its essential amino-terminal palmitoyl adduct. Transporters typically act by moving through a repeated cycle of conformational changes. If PTCH1 transport function employs such a conformational cycle, an agent that preferentially binds and stabilizes a specific PTCH1 conformation would be expected to disrupt its conformational cycle and transport activity, thus permitting activation of SMO. Such an agent thus may serve as a pathway modulator that could make lipid modifications dispensable and can shed light on conformational changes that occur during the PTCH1 working cycle.

Results

Development of a conformation-specific nanobody that activates pathway. Nanobodies are single-chain antibody fragments that have been used to stabilize specific GPCR protein conformations, and are amenable to genetic engineering. We have chosen as a starting point a synthetic yeast display library to select for conformation-specific nanobodies against PTCH1. To select conformation-specific nanobodies we first introduced conformational bias in PTCH1 by altering three acidic residues buried within its transmembrane domain (D499N, D500N, E1081Q, termed PTCH1-NNQ). These acidic residues, conserved within the RND transporter family, are required for PTCH1 activity in sterol transport and SMO regulation and are more generally proposed to drive conformational changes in RND transporters in response to cation influx (FIG. 1A). We thus reasoned that alteration of these residues in PTCH1 might affect the relative representation of its conformational states.

Figures 5A, 5B, 5C, 5D:
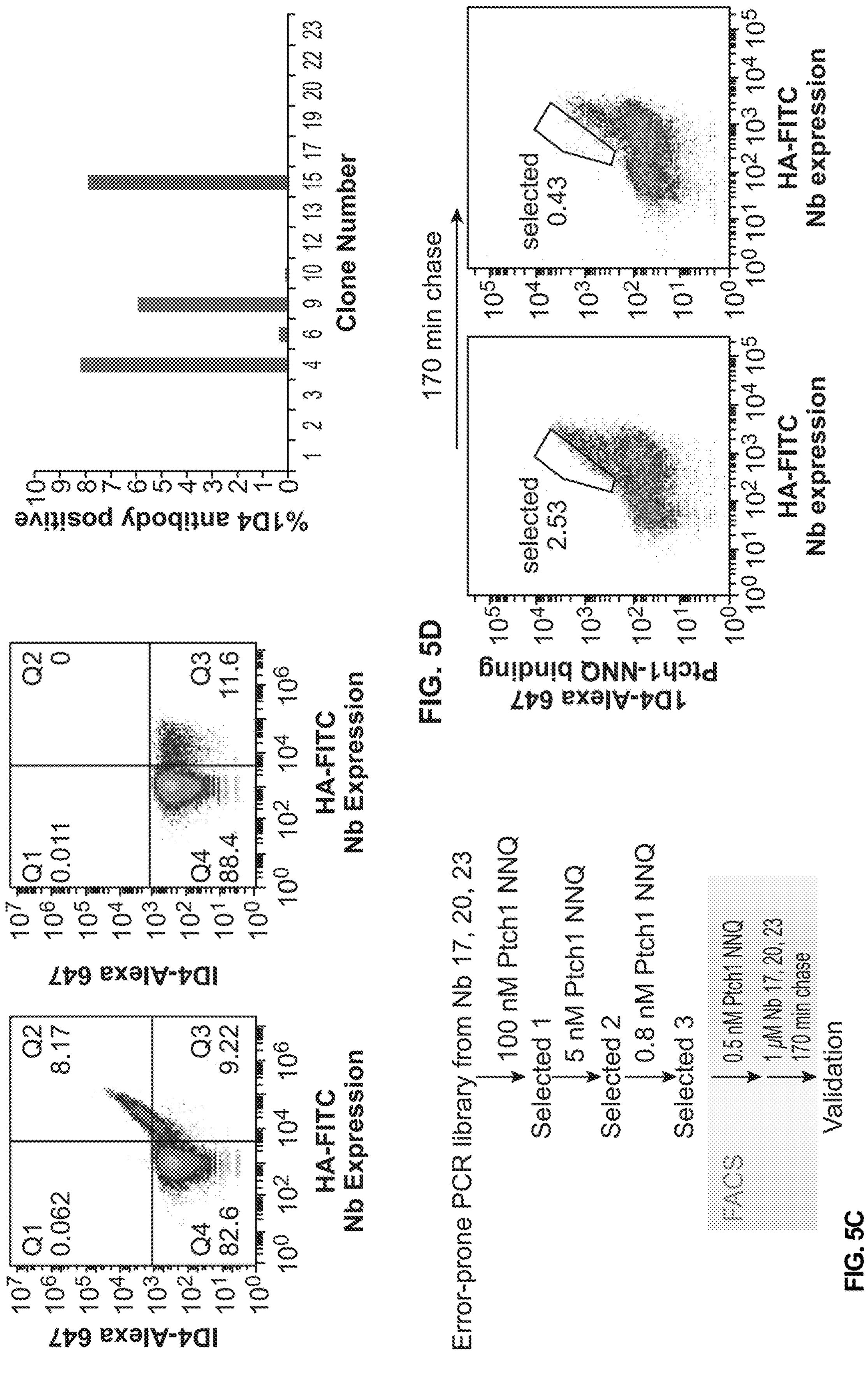

We used purified PTCH1-NNQ variant protein for selection of nanobody clones from the yeast display library. After several rounds of enrichment for PTCH1-NNQ binding yeast clones, we selected nanobodies that preferentially bind to PTCH1-NNQ versus wild-type PTCH1, using FACS (Fluorescence Activated Cell Sorting) and wild-type and NNQ PTCH1 proteins labeled with antibodies coupled to different fluorophores (FIG. 1B). Yeast cells expressing preferentially-bound nanobodies form a population off the diagonal of the FACS plot (FIG. 1C). After selecting nanobody-expressing yeast cells in the NNQ-preferring population, 15 unique clones were identified by sequencing, of which three were discarded because they bind directly to the antibody used during selection (FIG. 5A, B). As PTCH1 and PTCH1-NNQ differ only in the acidic residues in the transmembrane domain, differences in nanobody binding most likely derive from differences in conformational states between PTCH1 and PTCH1-NNQ.

Figure 1G:
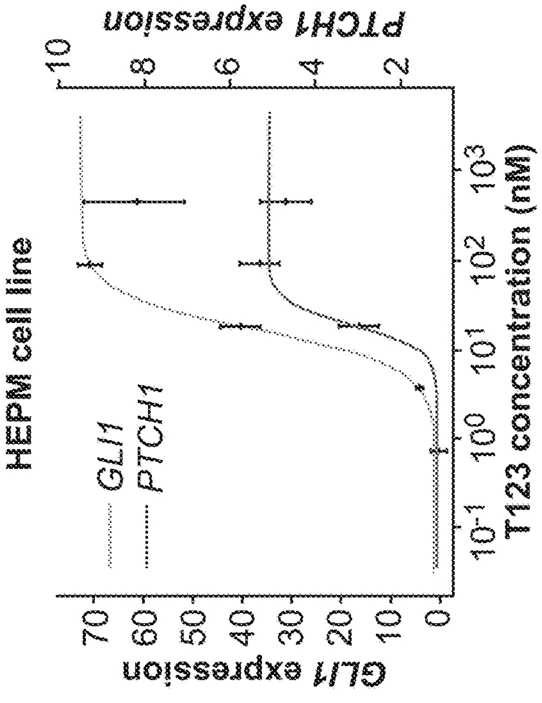
Figure 1H:
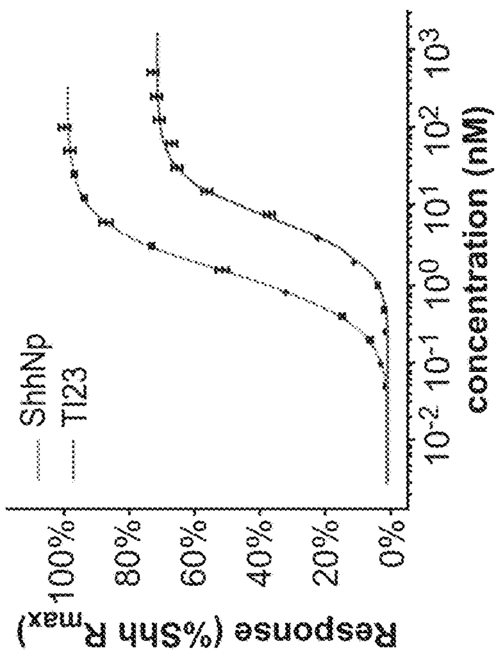

Stabilization of a specific PTCH1 conformation would be expected to inactivate its transport activity and permit downstream response in the Hedgehog pathway. We therefore tested the activity of purified nanobody proteins on 3T3-Light2 cells, using a Gli-dependent luciferase assay. Clones 17, 20, and 23 showed weak activation effects (FIG. 1D). We enhanced signaling potency through two rounds of affinity maturation, first by selection from an error-prone PCR library (FIG. 5C, D), and then from a library targeting the complementarity-determining regions (CDRs) using one-pot mutagenesis (FIG. 5E, F). The first round of affinity maturation yielded a series of nanobody clones deriving from clone 23 (SEQ ID NO:10) ("NB23") with H105R, G106R substitutions in CDR3 and several variant residues at G50 in CDR2. Among these variants, only the G50T substitution (named T23), could be expressed for purification from *E. coli*. T23 showed better potency in Gli-dependent luciferase assays than its Nb23 parent (FIG. 1E), and was used as the starting sequence for a second round of affinity maturation, in which all CDR residues were systematically randomized in one-pot mutagenesis. After selection based on PTCH1 binding, Y1021 in CDR3 was enriched, as well as T77N, an unintended substitution (FIG. 5G). This variant, named "TI23" (SEQ ID NO:23), was purified for further characterization, and it exhibited greater potency in pathway activation than its T23 parent (FIG. 1E). All of the nanobody variants showed preferential binding for PTCH1-NNQ, as revealed by two-color staining of yeast cells expressing these variants (FIG. 1F; FIG. 5H). TI23 also strongly activated human Hedgehog pathway targets GLI1 and PTCH1 at low nanomolar concentrations when tested in a cell line derived from human embryonic palatal mesenchymal (HEPM) (FIG. 1G). In comparison with ShhNp, TI23 exhibited similar potency, but consistently lower efficacy. The maximum response induced by TI23 is ~75% of that from ShhNp, suggesting that it is a partial agonist (FIG. 1H).

Figure 2A:
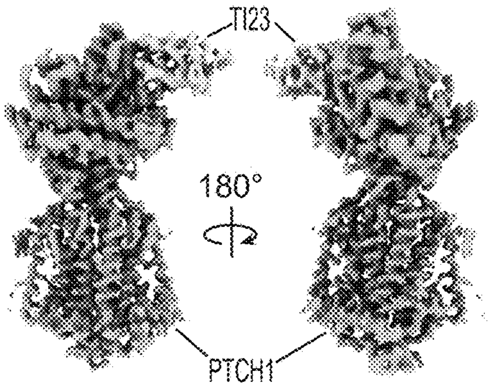
FIG. 2A-2F. Overview of mouse PTCH1::TI23 complex structure.
Figure 6E:
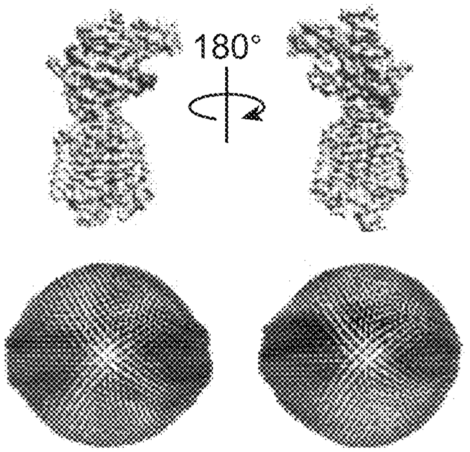
Figure 6F:
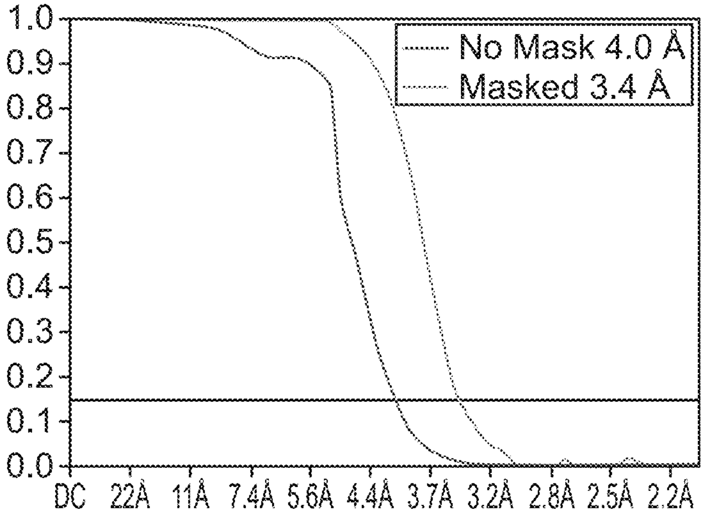
Figure 6G:
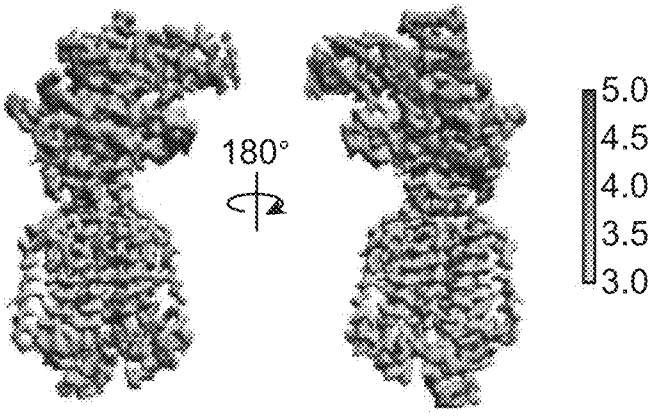

Structure of the PTCH1::TI23 complex. To determine the conformational effects of TI23 binding to PTCH1 we prepared the PTCH1::TI23 complex for structure determination by cryo-EM. The complex was clearly visualized in cryo-EM micrographs (FIG. 6A), with well-fitted contrast transfer function parameters (CTF; FIG. 6B) and 2D class averages (FIG. 6C). 3D reconstruction of a cryo-EM dataset yielded a high quality map (FIG. 2A; procedure in FIG. 6D) at a resolution of 3.4 Å (FIG. 6F). All 12 transmembrane (TM) helices and two major extracellular domains (ECDs) were resolved (FIG. 2A), and an atomic model of the PTCH1::TI23 complex was built based on this map and the previously determined murine PTCH1 structure (24). Most of the intracellular sequence was unresolved, and not modeled, except for two transverse helices preceding TM1 and TM7 (FIG. 2B).

Figure 2B:
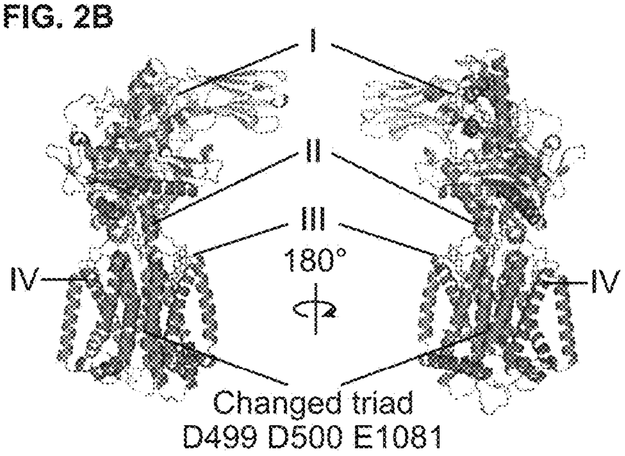

Sterol-like densities were identified in multiple sites, one in a pocket at the distal tip of ECD1 (farthest from the membrane, density I), one in the cavity proposed as part of the transport conduit (II) and two more at the periphery of the transmembrane domain (III and IV) (FIG. 2B). The density in site II is especially well resolved, and its unusual "Y" shape strongly suggests that sterol-like densities are also most likely GDN, but only the steroidal moiety of GDN, digitogenin, was resolved and modeled.

Figure 2C:
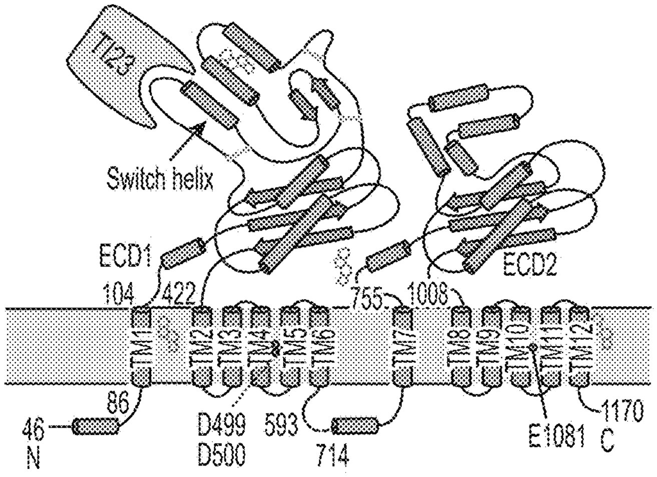
Figure 2D:
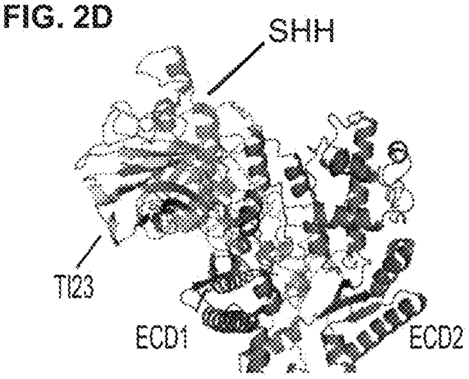
Figure 2E:
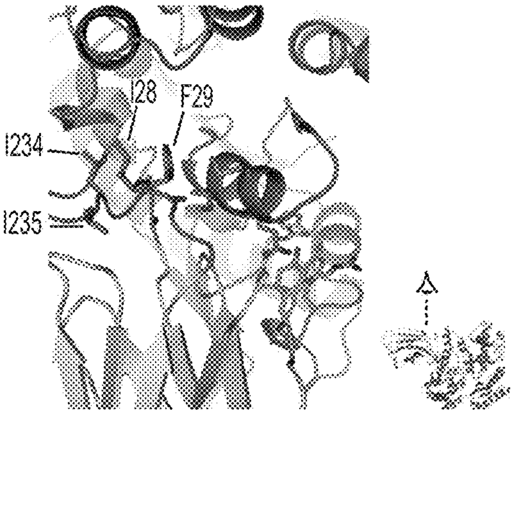
Figure 2F:
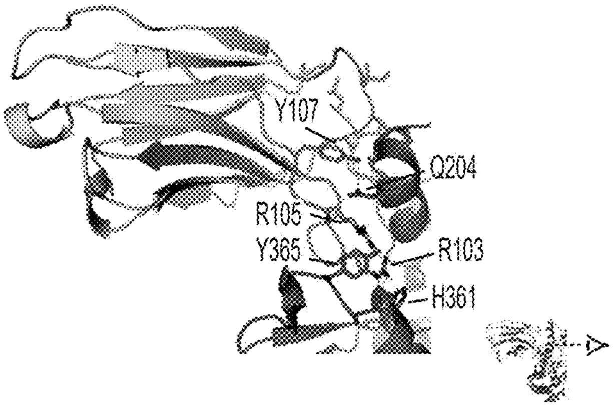

The nanobody interacts only with ECD1 of PTCH1, as shown in the schematic drawing (FIG. 2C). The binding site of TI23 overlaps with that of SHH, but SHH interacts with both ECD1 and ECD2 (FIG. 2D). The CDR1 and CDR3 loops of the TI23 nanobody contact a short helix in the PTCH1 ECD1 (the "switch helix", highlighted in FIG. 2C) from different angles. CDR1 interacts with PTCH1 by inserting hydrophobic residues 128 and F29 into the hydrophobic pocket at lipid site I (FIG. 2E), whereas CDR3 primarily forms a hydrogen bond network with other residues on the surface of PTCH1 (FIG. 2F).

Figure 7A:
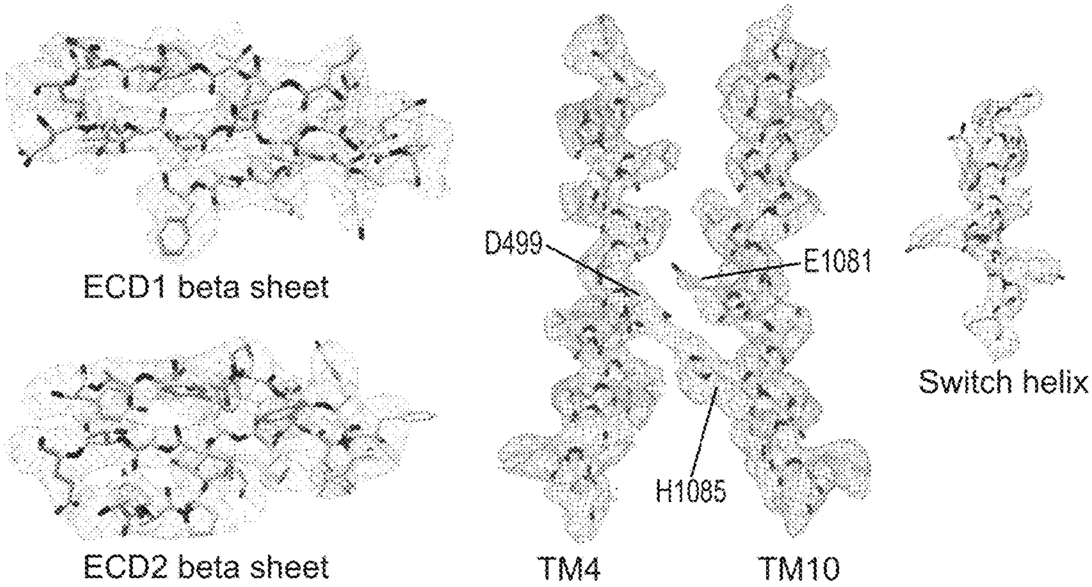
FIG. 7A-7D. Features of the protein model.
Figure 7B:
Figure 7C:
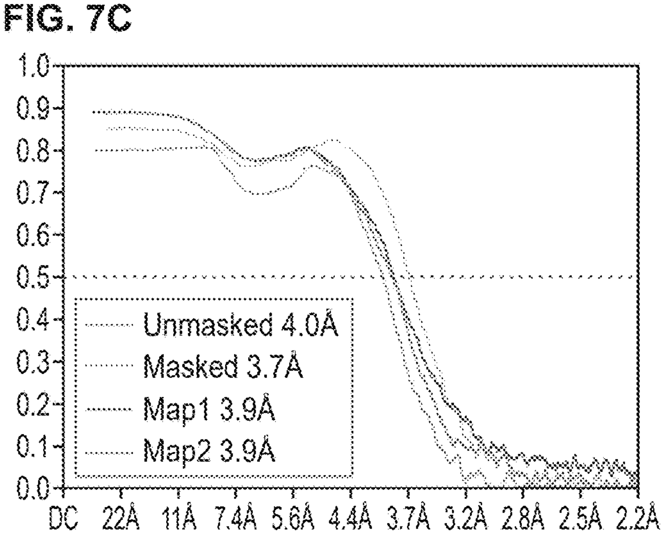
Figure 7D:
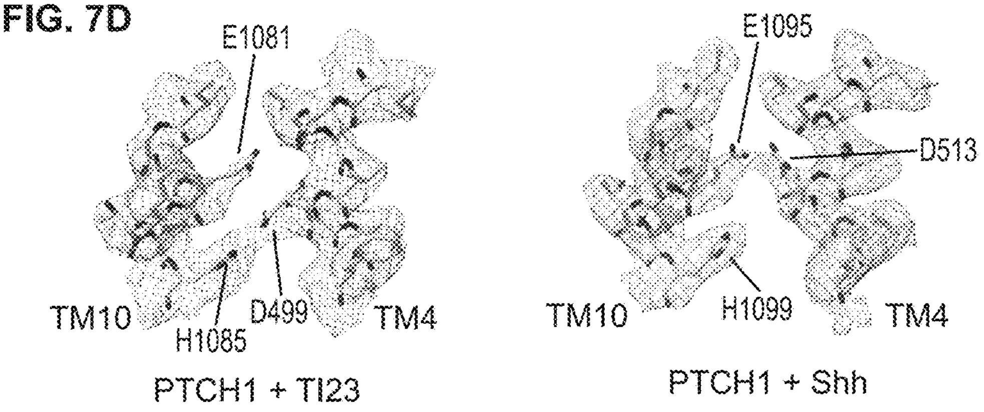

Although TI23 interacts exclusively with ECD1, we noted significant improvement in the resolution of side chains within the transmembrane domain. Of particular interest, the charged residue triad within TM4 and TM10 that was altered for selection of TI23 is better resolved than in most of the other published PTCH1 structures. We thus note that TM4 and TM10 in the PTCH1::TI23 complex associate with each other via a salt bridge between H1085 and D499, whereas in the SHH-bound PTCH1 structure, this interaction is disrupted (FIG. 7D). This nanobody-associated change in transmembrane domain side chain interactions suggests potential allostery between the ECD and the transmembrane domain.

The overall structure of the PTCH1::TI23 complex is similar to the unbound murine PTCH1 structure, with a root mean square deviation of 0.955A of the Ca carbon atoms over 910 residues. Both ECD1 and ECD2 display some conformational differences in the complex. One minor difference is a rotation of ECD2 around its connection to the TM domain by ~5 degrees towards ECD1 as compared to PTCH1 alone (FIG. 3A). A more marked difference is the rotation by ~32 degrees of the distal end of the "switch helix" within ECD1 towards the membrane in a manner suggestive of a flipped switch (FIG. 3A, inset). We refer to conformations of the switch helix in PTCH1 alone and in the PTCH1::TI23 complex as poses 1 and 2, respectively (FIG. 3A, inset). These two alternative poses of the switch helix are present but have gone largely unremarked in other structures of PTCH1 determined under various conditions. For example, in the ternary complex of a single native Shh ligand bound to two human PTCH1 molecules (23), PTCH1 from chain A, the molecule whose sterol conduit is occluded by interaction with the N-terminal palmitoyl moiety of the SHH ligand, adopts pose 2, whereas PTCH1 from chain B adopts pose 1. Indeed, in all published structures of PTCH1 the switch helix adopts one or the other of these two poses, suggesting that they represent discrete alternative conformations preferentially populated within the PTCH1 activity cycle (FIG. 3B). It is noteworthy that in the best-resolved SHH-PTCH1 structure, the switch helix in the extracellular domain adopts pose 1 while the salt bridge between H1085 and D499 in the transmembrane domain is broken. PTCH1::TI23 complex, in contrast, adopts the alternative conformation in both of these sites (FIG. 7). These changes are consistent with allostery between the charged residues in transmembrane domain and the switch helix in the extracellular domain. None of the other PTCH1 structures have clearly resolved side chains for the charged residues in TM4 and TM10, precluding further comparison.

Figure 8A:
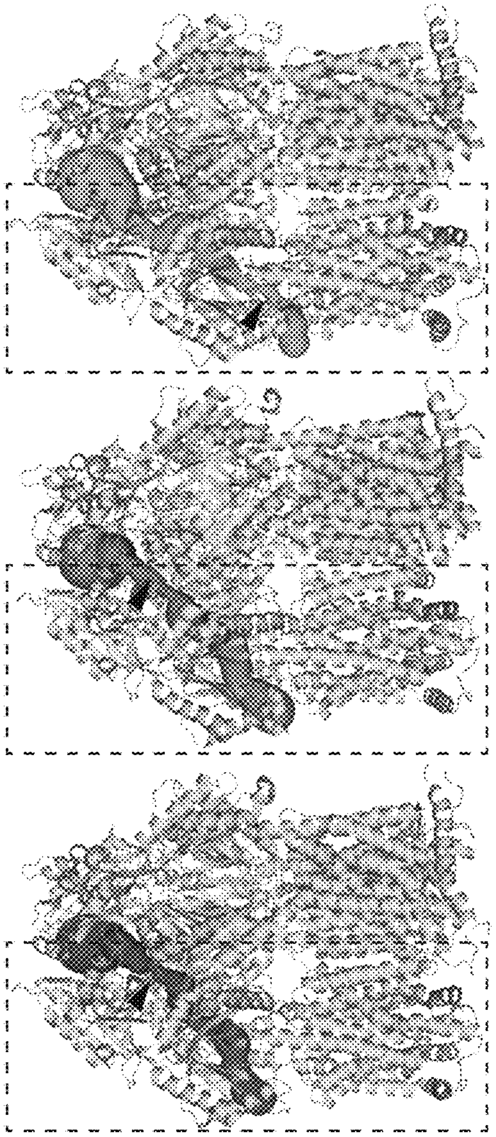
FIG. 8A-FIG. 8B. Comparison of AcrB and PTCH1 conformational changes (FIG. 8A) Two distinct sites (marked by triangles, one lower site close to the membrane plane and one upper site close to the upper exit of the extracellular domain) alternatively open and close in three distinct conformations of AcrB (PDB ID: 2gif, L state shown in chain A, T state shown in chain B, O state shown in chain C).
Figure 8B:
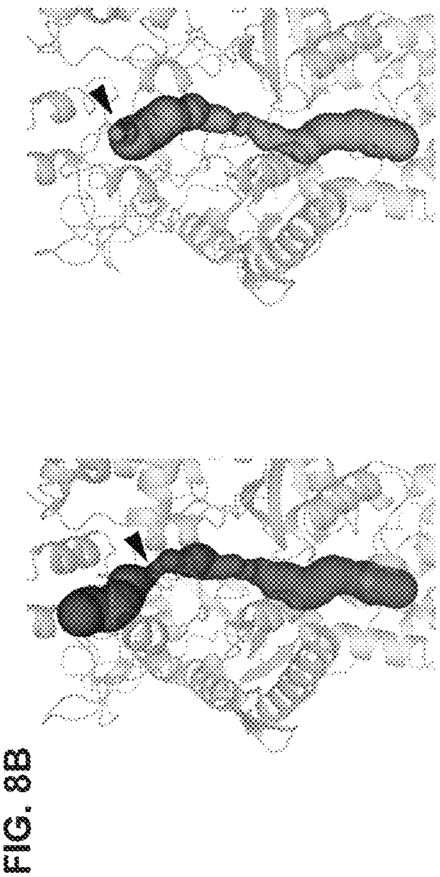

Effects of the switch helix on the sterol conduit. These structural rearrangements alter the shape of the transport conduit as assessed by the Caver program (FIG. 3C). The region of the conduit encompassing sterol I in murine PTCH1 thus is seen to be dramatically constricted in the conduit of the PTCH1::TI23 complex, and the conduit in the PTCH1::TI23 complex also acquires a distal opening to the exterior (FIG. 3D). In parallel with this change in conduit shape, the bound sterol-like density shifts from a more proximal enclosed cavity to a more distal position with an opening to the exterior (FIG. 3E). This concerted proximal constriction and distal expansion results primarily from rotation of the switch helix. If PTCH1 activity is, like other RND family members, driven by a chemiosmotic gradient, the conformational change identified here may form part of a defined sequence that results in directional movement of substrates within the transport conduit conformational transitions that affect the substrate conduit, similar in principle although distinct in detail from that of PTCH1. By analysis with the Caver program, a lower and an upper site in AcrB open and close alternatively to enforce directional movement of substrates (FIG. 8A) (34) whereas only a single upper site has been identified from PTCH1 structures (FIG. 8B).

The TI23 nanobody appears to stabilize pose 2 of the PTCH1 switch helix. If PTCH1-mediated transport of sterols away from the inner leaflet indeed depends on the dynamic changes in the shape of the conduit associated with switch helix movement, TI23 binding may lock PTCH1 in a state that is incompatible with sterol movement. To test this idea, we utilized a solvatochromic fluorescent sterol sensor, microinjected into cells to permit ratiometric measurement of sterol available for sensor binding within the inner leaflet of the membrane (35). This sensor previously revealed that available sterol decreases sharply with PTCH1 activity, and that PTCH1 inactivation by Shh ligand causes a return to normal sterol availability (24). Similar to the effect of Shh ligand addition, we noted that TI23 addition reversed the PTCH1-mediated reduction in cholesterol activity (FIG. 3F).

In vivo activation of the Hedgehog pathway. A small protein such as a nanobody (~12 kDa), might be expected to display excellent tissue penetrance and be readily accessible to cells in most tissues. We tested the activity of TI23 by intravenously injecting mice with adeno-associated virus (AAV) engineered to express it. This experiment should permit observation of biological effects elicited by sustained nanobody exposure as AAV infection is maintained over several weeks. We monitored lingual epithelium and skin, as these tissues display well-characterized responses to Hedgehog pathway activation.

Figures 4A, 4B, 4C:
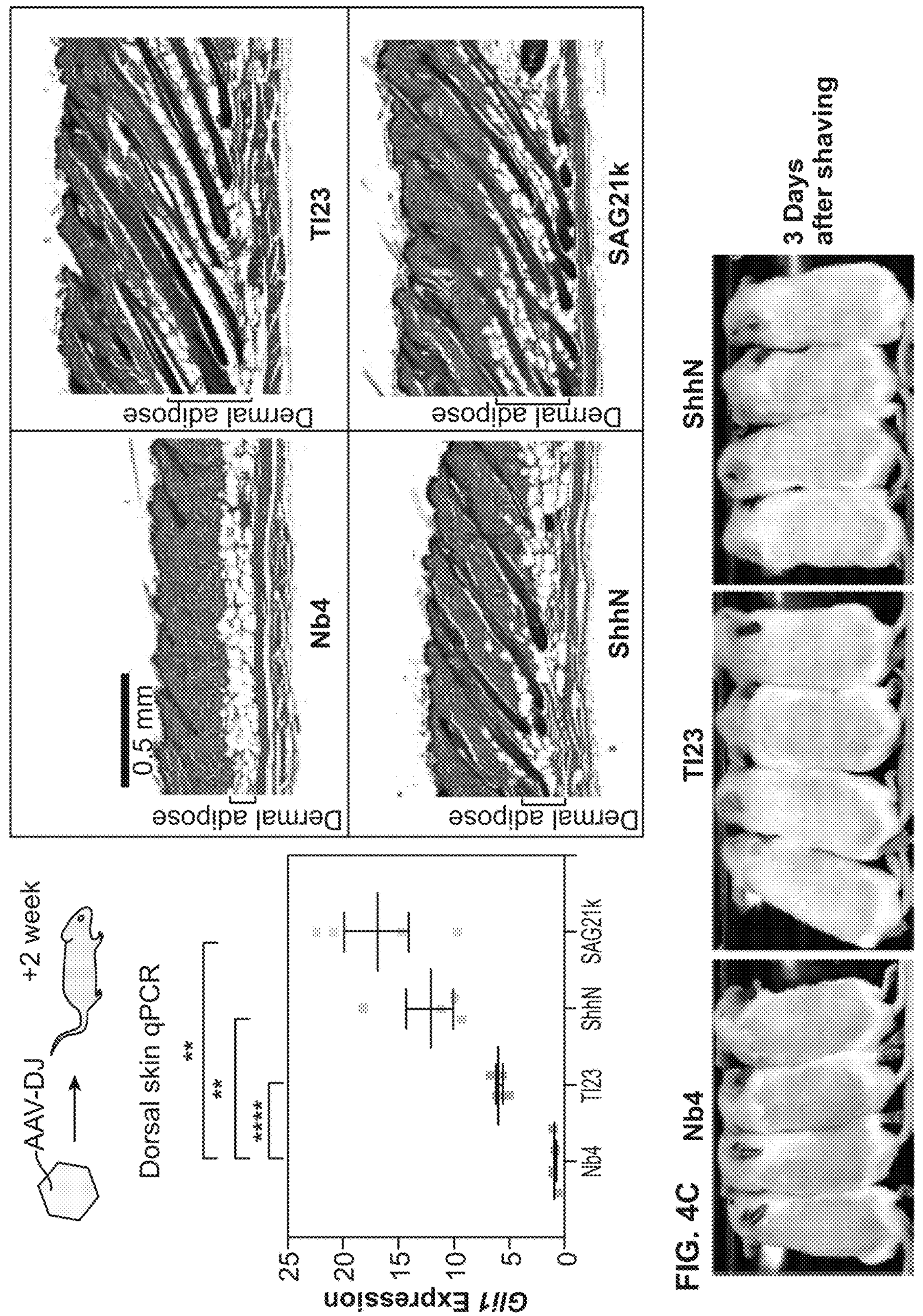
FIG. 4A-4C. Validation of TI23 activity in the skin.

The TI23 nanobody augmented Hedgehog pathway activity in the dorsal skin, as indicated by a 6-fold increase in Gli1 RNA levels (FIG. 4A). The effect from TI23 is weaker than ShhN or SAG21k, consistent with the observation that TI23 works as a partial agonist in vitro. We also noted expansion of hair follicles into the dermal adipose layer upon histological examination of dorsal skin in mice infected with AAV encoding TI23 or ShhN, but not a control nanobody (Nb4), indicating hair follicle entry into the anagen phase of the hair cycle (FIG. 4B). Consistent with accelerated entry into anagen, we noted faster hair regrowth on the dorsal skin after shaving (FIG. 4C).

Figure 4D:
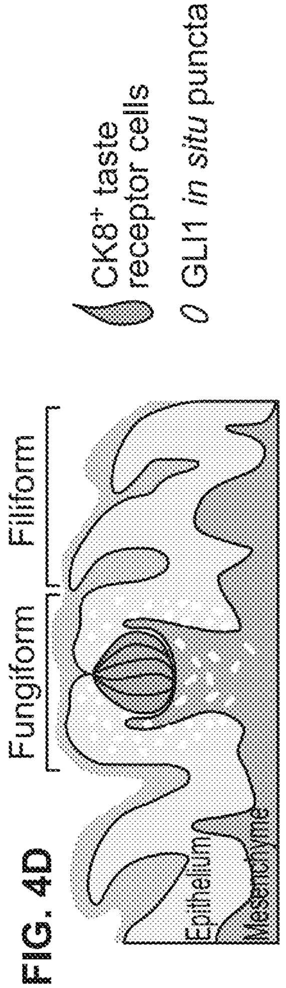
(FIG. 4D) Schematic view of the dorsal tongue surface. The cells with active Hedgehog pathway response under physiological conditions are primarily located within the fungiform papillae (FIG. 4E) TI23 induced Gli1 expression in lingual epithelial cells located in the fungiform and filiform papillae, as indicated by in situ hybridization using RNAScope. Animals receiving AAV-DJ encoding control nanobody (Nb4), TI23 or ShhN were sacrificed 2 weeks after injection. With pathway agonists TI23, ShhN, or the small molecule SAG21k, the expression of Gli1 increased in both fungiform papillae containing taste receptor cells ($Ck8^{+}$, red), and filiform papillae, as shown in the inset panels. For each group, n=4.
Figure 4F:
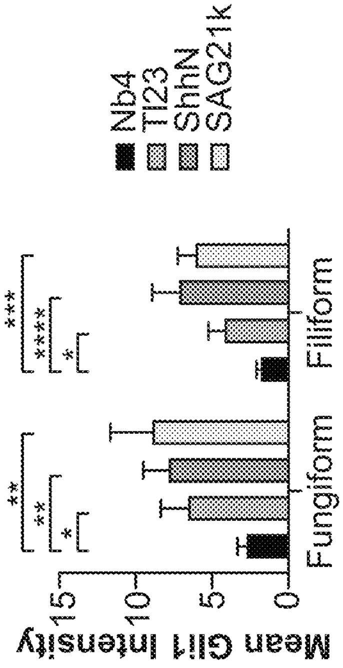
(FIG. 4F) The mean fluorescence intensity of Gli1 is compared among regions of fungiform and filiform papillae. One-way ANOVA with Tukey's multiple comparison suggests that TI23, ShhN, or the small molecule SAG21K, the expression of GLI1 increased levels compared to the control conditions. *, $p<0.05$; , $p<0.005$; *, $p<0.0005$; ****, $p<0.0001$. For fungiform regions, n=5, 3, 4, 4 for Nb4, TI23, ShhN, SAG21k, respectively. For filiform regions, n=5, 4, 3, 5, for Nb4, TI23, ShhN, SAG21k, respectively.
Figure 4E:
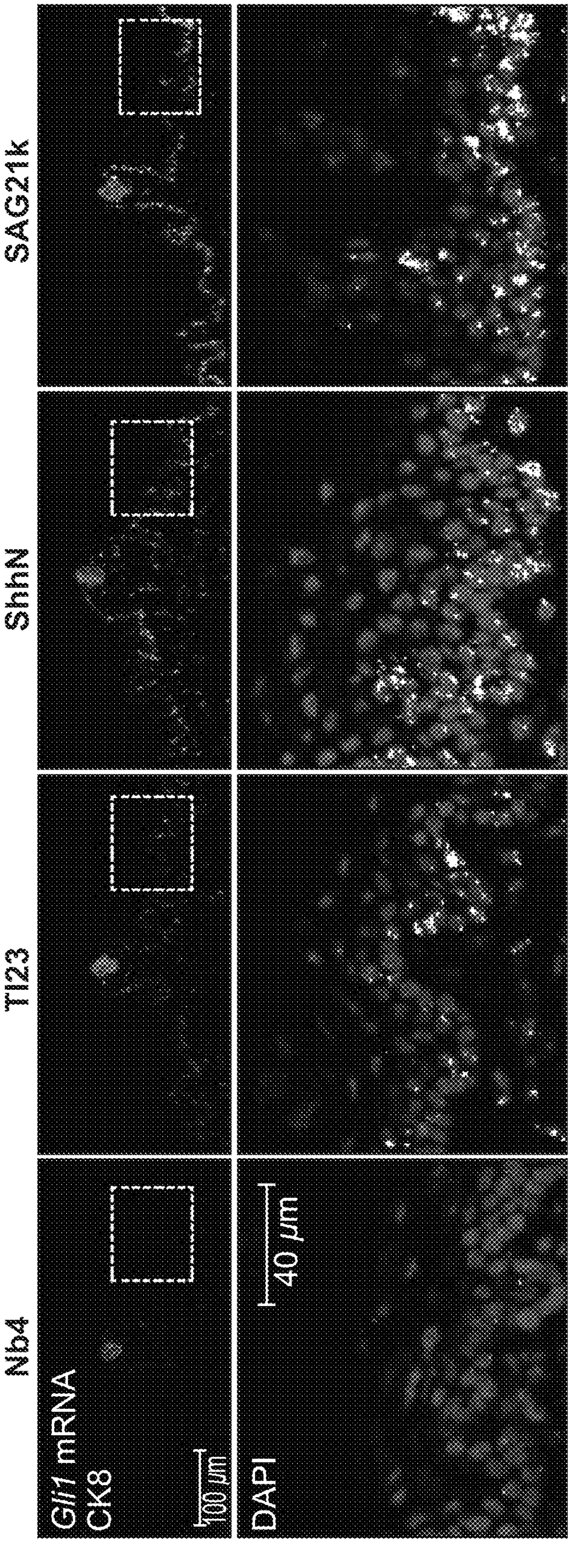

We also examined Gli1 mRNA by fluorescence in situ hybridization (FISH) as an indicator of pathway activation in lingual epithelium. Hedgehog pathway activity is limited to the cells surrounding the $CK8^{+}$ taste receptor cells in untreated animals (FIG. 4D). In ShhN or TI23-virus injected mice, the range of Hedgehog pathway activity, as indicated by Gli1 expression, expanded dramatically as compared to the animals that received the control virus (FIG. 4E,F). A similar expansion of Gli1 expression was also noted in mice given SAG21k (FIG. 4E,F), a small molecule Hedgehog agonist that activates SMO.

The therapeutic applications of Hedgehog pathway modulation have focused primarily on pathway antagonists, and inhibition of the Hedgehog pathway has proven efficacious in the treatment of cancers driven by excessive Hedgehog pathway activity directly in primary cells of the tumor. In contrast to promoting tumor growth, however, pathway activity recently has been found to suppress cancer growth and progression when it occurs in stromal cells rather than primary cells, particularly in cancers of endodermal organs, such as bladder carcinoma, and colon and pancreatic adenocarcinoma. Pathway activation may also confer therapeutic benefits in regeneration of taste receptor cells of the tongue, which are often lost or diminished in chemotherapy patients, in protection or recovery from diseases such as colitis, reduction of tissue overgrowth in prostatic hypertrophy, or acceleration of bone healing in diabetes.

Despite these potential benefits, pathway activation in clinical settings is hindered by the lack of means to target specific tissues. Available Hedgehog pathway agonists are all hydrophobic in nature, including small molecule members of the SAG family, certain oxysterols, and purmorphamine, all of which target SMO, and the lipid-modified Hedgehog protein or its derivatives, which target PTCH1. Our conformation-selective PTCH1-directed nanobody TI23 (SEQ ID NO:23) represents a new class of potent, more hydrophilic agonists, which unlike the native Hedgehog protein does not require hydrophobic modification for activity. TI23 furthermore has the potential to be engineered for targeting by fusion to an antibody or other agent with tissue or cell-type specificity. These engineered variants may avoid pleiotropic effects from systemic pathway activation and be better suited for clinical applications.

TI23 is useful for further pharmaceutical development, and also provides insight into the PTCH1 transport mechanism. Directional movement of substrate through a transporter protein implies conformational change, but the identification of such conformational transitions for transporters is a nontrivial challenge. Our conformation-specific nanobody approach allowed us to identify two distinct conformations associated with poses 1 and 2 of the PTCH1 switch helix. The changes in shape of the transport conduit associated with these poses suggest peristaltic movement as a potential mechanism for directed substrate movement. As PTCH1 is distinct from the well-characterized RND transporter AcrB in both its preferred substrate and its extracellular domain structure, it is not surprising that the conformational transitions of these proteins differ. Indeed, given these differences, the apparent similarity in peristaltic movement of the substrate conduit in both proteins seems quite remarkable.

TI23 binding to PTCH1 would be expected to induce a conformational change similar to that of PTCH1-NNQ. As the altered residues in NNQ are buried in the transmembrane domain whereas TI23 binds to the extracellular domain, the most parsimonious explanation is allostery between the two domains. In bacterial transporters, a charged triad in TM4 and TM10 conducts protons across the membrane to extract energy from a chemiosmotic gradient. In PTCH1, two distinct states of this triad of charged residues have now been observed. In the SHH bound structure, D513 and E1095 are close to each other and their negative charges may be stabilized by a bound cation, whereas in the TI23 bound structure, these two residues are far apart, most likely not interacting with any cations. This difference is consistent with the potential effect of NNQ alterations on cation binding, as the lack of charge neutralization in PTCH1-NNQ would be expected to greatly weaken the cation interaction.

An interesting aspect of the TI23 nanobody is that it works as a partial agonist, whereas PTCH1-NNQ variant exhibits little activity in cells. One explanation for this difference may be that the nanobody may tolerate a small degree of conformational flexibility, thus permitting a low level of PTCH1 transport activity. Indeed, in the local resolution map, resolution of the nanobody region is much worse than the rest of the protein, suggesting substantial structural heterogeneity.

Further in vitro evolution to improve structural stability of the nanobody may augment its efficacy to activate the pathway. Our conformation-selective nanobody approach can be generalizable to the study of other transporters, in particular other members of the RND family. In mammals this family includes the NPC1 cholesterol transport protein, and other PTCH-like proteins, such as PTCHD1, disruption of which is strongly associated with autism. For other transporters, mutations that disrupt function may do so by biasing the normal conformational landscape without uniquely stabilizing any one conformation. Selection of nanobodies that preferentially bind such mutants may enable capture of sparsely populated yet critical conformations, expanding the repertoire of experimentally accessible states for structural and functional studies and providing pharmacologic agents with the potential to be targeted to specific cell types or tissue compartments.

Materials and Methods

Cell culture. Sf9 and 293T cells were maintained in culture according to previously published conditions. 293-Freestyle cells were maintained in suspension culture in an 8% $CO_2$ incubator equipped with a shaking platform, using Freestyle 293 expression medium (Life Technologies) supplemented with 1% fetal bovine serum (Gemini Bio). Baculovirus production in Sf9 cells and infection of suspension 293 cultures with recombinant baculovirus (BacMam expression) was performed as previously described.

Molecular cloning. All constructs were cloned with Gibson assembly. For BacMam expression, PTCH1 variants were cloned into pVLAD6 vector. For yeast selection, Ptch1-C and Ptch1-C-NNQ variants were used. Ptch1-C is mouse PTCH1 truncated at amino acid 1173, deleted at 619-711 and altered at C1167Y. Use of Ptch1-C for selection minimized the possibility of getting nanobodies that bind to PTCH1 intracellular domain, due to extensive deletion of the intracellular sequence. For structural determination and cell biology experiments, Ptch1-B as reported earlier was used. For luciferase assay and cell surface binding experiments, PTCH1 variants were cloned into pcDNA-h (pcDNA3 vector with the neomycin resistance cassette removed).

Yeast display selection. The synthetic nanobody library was grown in SDCAA media at 30 C to a cell density of ~$1\times10^8$/ml. Cells covering about 10 times the initial diversity ($5\times10^8$ diversity, $5\times10^9$ cells) were transferred into SGCAA media at 20C to induce expression of nanobody on cell surface. For selection, $7.5\times10^9$ cells were pelleted by centrifugation and resuspended in selection buffer (20 mM HEPES, pH 7.5, 150 mM NaCl, 0.5 mg/ml BSA, 0.1% DDM, 0.02% CHS). The cells were then incubated with 100 nM 1D4-tagged Ptch1-C NNQ, spun down and washed with selection buffer, and then with FITC-labeled 1D4 antibody, then 100 μL anti-FITC MACS beads. After loading the beads-bound cells onto the magnetic manifold and washed extensively with selection buffer, the bound cells were eluted, cultured in SDCAA media and induced for nanobody expression in SGCAA media. A second round of selection was then performed on these cells, first with the Alexa647 labeled 1D4 antibody alone to counter-select antibody-binding cells and then with 100 nM 1D4 tagged Ptch1-C NNQ. The selected cells were grown in SDCAA and induced with SGCAA again and then incubated with 100 nM Myc-tagged Ptch1-C and 100 nM 1D4-tagged Ptch1-C-NNQ and stained with anti-Myc Alexa 647 and anti-1D4 FITC and cells showing stronger FITC signal on FACS were selected. The same FACS selection was repeated and the selected cells were grown and dilution-plated. Plasmid was prepared from single colonies and sequenced after rolling cycle amplification (RCA). 15 unique sequences were retrieved from 24 colonies. Yeast cells harboring these nanobody sequences were then tested for binding to anti-1D4 antibody and to Ptch1-C-NNQ. Three out of 15, Clone #4, #9 and #15, bind to 1D4 antibody directly. Clone 4 was used as a control nanobody in activity characterizations. The rest of the sequences were cloned into pET26b vectors for expression and purification from *E. coli.*

Nanobody purification. pET26b vectors containing nanobody sequences were transformed into *E. coli* BL21 (DE3) strain. The bacteria were grown in Terrific broth media at 37° C. to OD600 of 0.8, and then induced with 0.2 mM IPTG and transferred to 20° C. After overnight expression, the cells were harvested by centrifugation at 8,000 g. The cell pellet was resuspended in SET buffer (500 mM sucrose, 0.5 mM EDTA, pH 8.0, 200 mM Tris, pH 8.0) at a ratio of 5 ml buffer/1 g pellet. After stirring for 30 min at room temperature, two volumes of water was added. After stirring for an addition 45 min, $MgCl_2$ was added to 2 mM and benzonase at 1:100,000. After 5 min incubation, NaCl was added to 150 mM, imidazole to 20 mM and the whole mixture was centrifuged at 20,000 g for 15 min at 4 C. The supernatant was then loaded onto a Ni-NTA column, washed with ice-cold buffer (20 mM HEPES pH 7.5, 500 mM NaCl, 20 mM imidazole) and then eluted in 20 mM HEPES pH 7.5, 150 mM NaCl, 250 mM imidazole. The eluted protein was then dialyzed overnight in 20 mM HEPES pH 7.5, 150 mM NaCl at 4° C. All of the initial hits except for clone 13 could be expressed and purified. Clone 13 was then excluded from analysis.

Affinity maturation. The first round affinity maturation library was made with error-prone PCR. Nanobody clone 17, 20 and 23 were chosen as the starting point of this selection. 10 ng plasmid containing the nanobody sequence was used as the template (equivalent to ~1 ng DNA of nanobody sequence) and PCR amplified with Mutazyme kit. The PCR product was gel-purified and 10 ng was then used as the template for the next round of PCR. A total of 4 rounds of PCR were performed. The final product was then amplified with Phusion polymerase to obtain sufficient amounts for yeast transformation. A total of ~100 μg DNA was purified for each parental sequence using ~2 μg of the error-prone PCR product. The DNA fragments were then transformed into yeast along with pYDS2.0 plasmid backbone. DNA from 3 different parental sequence, and a mixture of the three were electroporated separately into yeast cells, but the cells were pooled in YPD for recovery after electroporation. Serial dilution and plating gave an estimate of $1\times10^9$ independent transformant for this library. The transformed yeast cells were then grown in YPD media with 100 μg/ml nourseothricin sulfate, and then induced in YPG media with the same antibiotic. The yeast cells were enriched for PTCH1 binding by MACS selection using concentrations of 1D4-tagged Ptch1-C NNQ at 100 nM, 5 nM, 0.8 nM. Then cells expressing nanobody were incubated with Ptch1-C NNQ at 0.6 nM. After washing in selection buffer, the cells were incubated with the parental 17, 20, 23 nanobody proteins at 1 μM each for 170 min at room temperature. The cells were then stained with FITC-labeled HA antibody to mark nanobody expression levels and Alexa 647-labeled anti-1D4 antibody to mark PTCH1 binding. Cells that maintain high PTCH1 binding were selected from FACS. 64 clones were sequenced to identify repeating changes.

The second round of affinity maturation was performed with a library targeting the complementarity determining regions (CDRs) using the one-pot mutagenesis method. A pool of DNA oligos with NNK substituting each codon in the CDR regions was used for one-pot mutagenesis of the CDRs so that theoretically all 20 amino acids at each position were represented in this library. The DNA product from one-pot mutagenesis was then amplified with Q5 polymerase and purified with gel extraction. A final product ~5 μg DNA was used for yeast transformation. The transformed cells were grown in YPD media containing 100 μg/ml nourseothricin sulfate and induced in YPG media containing the same antibiotic. The cells were then incubated with 10 nM protein C-tagged Ptch1-C, washed in selection buffer and then incubated with 1 μM 23T (purified nanobody protein with the consensus sequence from the 1st round of affinity maturation) for one day. The cells were then stained with FITC-labeled HA and Alexa 647 labeled anti-protein C antibody and the PTCH1-high cells were selected in FACS. The cells were grown in YPD and induced again. The same FACS selection procedure was repeated to further purify the population. The nanobody sequences from the plasmids prepared from the initial yeast library and the final selected library were then amplified with Q5 polymerase and sent for amplicon sequencing at MGH sequencing core.

PTCH1 purification. Purification of PTCH1 was performed as previously described with minor changes. Suspension 293 cells were grown to a density of $1.2-1.6\times10^6$/ml, supplemented with 10 mM sodium butyrate, and infected with high-titer Ptch1-SBP baculoviruses for 40-48 hr. Cell pellets were stored at −80° C. Pellets were thawed into hypotonic buffer (20 mM HEPES pH 7.5, 10 mM $MgCl_2$, 10 mM KCl, 0.25 M sucrose) supplemented with protease inhibitors and benzonase. Crude membranes were pelleted with centrifugation (100,000×g, 30 min., 4° C.). The pellet was resuspended in lysis buffer (300 mM NaCl, 20 mM HEPES pH 7.5, 2 mg/ml iodoacetamide, 1% DDM/0.2% CHS) with protease inhibitors and solubilized for 1 hour at 4° C. with gentle rotation. After centrifugation (100,000×g, 30 min., 4° C.), the supernatant was incubated with streptavidin-agarose affinity resin in batch mode for 2-3 hours at 4° C. with gentle rotation. The resin was packed into a disposable column, and washed with 20-30 column volumes of buffer (20 mM HEPES pH 7.5, 300 mM NaCl, 0.03% DDM/0.006% CHS). Protein was eluted in the same buffer supplemented with 2.5 mM biotin.

Cryo-EM data acquisition. Eluted Ptch1-B protein was mixed at 1:1.1 ratio with TI23 and then loaded onto Superdex 200 column pre-equilibrated with SEC buffer (20 mM HEPES, pH 8, 150 mM NaCl, 0.02% GDN). The peak fractions were collected and concentrated with an Amicon filter with molecular weight cutoff of 100 kDa to A280 ~4.5. 2.5 μL sample was applied to a glow-discharged quantifoil grid on a vitrobot. The sample chamber was kept at 100% relative humidity. The grid was blotted for 10s and plunged into liquid ethane bath cooled by liquid nitrogen. The cryo grids were imaged on a Titan Krios 2 electron microscope operated at 300 kV. Images were taken on the pre-GIF K2 camera in dose fractionation mode, at nominal magnification of 22.5k, corresponding to a pixel size of 1.059 Å (0.5295 Å per super-resolution pixel). The dose rate was ~8e/pix/see with a total exposure time was 12s at a frame rate of 0.2s/frame. Fully automated data collection was performed with SerialEM, with a defocus range of −1 μm to −3 μm. Gain reference was taken at the beginning of the data collection and was applied later in data processing.

Image processing. A total of 7,046 movie stacks were collected. The movie stacks were corrected by gain reference, binned by 2, and corrected for beam-induced motion with MotionCor2. CTF was determined with CTFFIND4 from the motion-corrected sums without dose-weighting using a wrapper provided in cryoSPARC2. Dose-weighted sums were used for all the following steps of processing. Particles were autopicked cryoSPARC2. Particles corresponding to protein molecules were selected from 2D classification. These particles were then reconstructed ab initio, and then classified with heterogeneous refinement into 3 classes, using two copies of the map generated from the last step plus one junk map as the initial models. The best class was chosen for homogeneous refinement and then non-uniform refinement to obtain a map at 4.1 Å. The particles were then analyzed with the 3D variability analysis tool and the two extremes of the first eigenvector were used as the basis for further 3D classification. The final 3D class was refined with non-uniform refinement to a resolution of 3.7 Å. The particle stack was then exported to cisTEM using the scripts in pyEM. After one iteration of local refinement with a mask excluding the detergent micelle, a map was reported at 3.4 Å. The final map after sharpening was used for model building.

Protein model building. Nanobody TI23 structure was generated with rosettaCM using 4mqtB and 5m30F as the template structures. The generated structure and the previously determined PTCH1 structure (6mg8) were docked into the cryo-EM map and refined in phenix.real_space_refine with morphing. The refined model was then edited manually in coot, to add in residues that are now resolved in the new structure, and the small molecules. The constraints for small molecules were generated on the PRODRG server. The entire structure was then refined in phenix.real_space_refine.

FACS-based ShhN binding assay. 293 cells were transiently transfected with GFP-tagged Ptch1 constructs. After 24 hours, cells were dissociated using 10 mM EDTA, washed with HPBS 0.5 mM $Ca^{2+}$, and pelleted by centrifugation. Cells were then resuspended in binding buffer (HPBS, 0.5 mM $Ca^{2+}$, 0.5 mg/ml BSA) and incubated with purified ShhN-biotin (1:400 dilution) for 30 minutes at 4° C. Cells were then washed three times in binding buffer by centrifugation and subsequently incubated with Alexa Fluor 647 streptavidin conjugate (Invitrogen) for 15 minutes at 4° C. Cells were then washed three times by centrifugation in wash buffer (binding buffer plus 1 mM biotin) and the percentages of cells bound by ShhN were quantified by flow cytometry after gating for PTCH1-GFP expression (BD FACSAria II, Stanford Stem Cell Institute FACS Core).

Gli-dependent luciferase assay. The luciferase assay was performed in Ptch1-/MEFs, as previously described. Ptch1+ MEFs were seeded into 24-well plates and then transfected with various plasmids along with a mixture containing 8×Gli firefly luciferase and SV40-*renilla* luciferase plasmids. For each well, 2 ng (0.4%) plasmid encoding Ptch1-B variants, or 5 ng (1%) plasmid encoding full-length PTCH1 was used. When cells were confluent, they were shifted to DMEM with 0.5% serum containing ShhN-conditioned medium or control medium and incubated for 48 hr. Luciferase activity was then measured using a Berthold Centro XS3 luminometer. The ShhN conditioned medium was prepared from 293 cells transfected with a plasmid expressing the amino signaling domain of Shh. In brief, 293 cells were transfected with the ShhN expression plasmid with lipofectamine 2000. Twelve hours after transfection, culture medium was replaced with 2% FBS low-serum medium. The conditioned medium was then collected 48 hours after medium change, and used at 1:10 for the luciferase assays.

Cellular cholesterol measurement. The Perfringolysin O D4 domain (a.a. 391-500) and mutants were expressed as $His_6$-tagged proteins in *E. coli* BL21 RIL codon plus (Stratagene) cells and purified using the $His_6$-affinity resin (GenScript). These proteins were labeled at the single Cys site (C459) by a solvatochromic fluorophore to generate ratiometric sensors. Ptch1−/− MEFs were seeded into 50 mm round glass-bottom plates (MatTek) and grown at 37° C. in a humidified atmosphere of 95% air and 5% $CO_2$ in Dulbecco's modified Eagle's medium (DMEM) (Life Technologies) supplemented with 10% (v/v) fatal bovine serum (FBS), 100 U/ml penicillin G, and 100 μg/ml streptomycin sulfate (Life technologies). After attachment to the culture vessels (~24 hr), cells were transiently transfected with plasmids encoding Ptch1-B variants using the jetPRIME transfection reagent (Polyplus Transfection) according to the manufacturer's protocol. 1 μg plasmid was used for each transfection. Cholesterol in the inner (IPM) leaflets of the plasma membrane was quantified using cholesterol sensors as described previously with some modification. Specifically, the Y415A/D434W/A463W (YDA) mutant of the D4 domain labeled with (2Z,3E)-3-((acryloyloxy)imino)-2-((7-

(diethylamino)-9,9-dimethyl-9H-fluoren-2-yl)methylene)-2,3-dihydro-1H-inden-1-one (WCR) was delivered into the cells by microinjection for quantification of IPM cholesterol ([Chol];). All sensor calibration, microscopy measurements, and ratiometric imaging data analysis were performed as described.

Mice. All procedures were performed under Institutional Animal Care and Use Committee (IACUC)-approved protocol at Stanford University. Wild-type FVB/NCrl (207) mice were purchased from Charles River. Male mice at seven week-old age were randomly assigned to groups of predetermined sample size. All experiments with direct comparisons were performed in parallel to minimize variability. Hedgehog agonist SAG21k was delivered by osmotic pump (Alzet) over the course of two weeks at a dose of 2 mg/kg/day.

Adeno-associated virus (AAV) production. The backbones of all AAV plasmids were based on pAAV-EF1a-Cre (Addgene, 55636) with poly (A) signal replaced with bGH. Nanobody sequences were cloned into the vector for expression in infected cells. AAVs were generated in HEK 293T cells and purified by iodixanol (Optiprep, Sigma; D1556) step gradients as described. Virus titers were measured by quantifying DNase I-resistant viral genome with qPCR using a linearized viral genome plasmid as the standard. Purified virus was intravenously injected into anesthetized mice at $1\times10^{11}$ μg per mouse or other specifically indicated titer through the retroorbital sinus.

Histology. Animals were euthanized and dorsal skin was excised for RNA extraction. Mice were then perfused with PBS and 4% paraformaldehyde (PFA) in PBS, and tongues and dorsal skin were post-fixed in 4% PFA for 24 hours. Tongues were processed for in situ hybridization according to RNAScope multiplex fluorescence kit (ACD systems) using mouse Gli1 probe (311001), followed by immunostaining as described. Immumofluorescence imaging was performed on laser scanning confocal microscopes (Zeiss LSM 800). Skin was processed for standard H&E staining by Animal Histology Service at Stanford University.

RNA extraction and qRT-PCR. Skin samples were homogenized and extracted for RNA using TRIzol, followed by RNeasy Mini Kit (QIAGEN) and DNase Set (QIAGEN). Gli1 and Hprt1 levels were determined by one-step quantitative reverse transcriptase PCR (qRT-PCR) on an ABI 7900HT instrument using SuperScript III Platinum One-Step System with TaqMan Gene Expression Assays (Gli1, Mm00494654_m1; Hprt, Mm00446968_m1; Thermo Fisher). Normalized expression levels relative to control group were compared using ordinary one-way ANOVA tests with Dunnett's multiple comparison correction.

TABLE 1

Summary of cryo-EM data collection and model refinement

| Parameter | Value |
|---|---|
| Data collection/processing | |
| Voltage (kV) | 300 |
| Magnification | 22,500 |
| Defocus range (μm) | −1.0 to −3.0 |
| Pixel size (Å) | 1.059 |
| Total electron dose $e^-/Å^2$) | 38 |
| Exposure time (s) | 12 |
| Number of images | 7,046 |
| Number of frames/image | 60 |
| Initial particle number | 3,621,265 (autopick) 1,402,887 (2D select) |
| Final particle number | 307,652 |
| Resolution (unmasked, Å) | 4.0 |
| Resolution (masked, Å) | 3.4 |
| Refinement | |
| Composition | |
| Number of atoms | 8,796 |
| Number of residues | 1,120 (protein) |
| Ligands | NAG: 7 Q7G: 4 |
| R.m.s. deviations | |
| Bond lengths (Å) | 0.004 |
| Bond angles (°) | 0.098 |
| Ramachandran | |
| Favored (%) | 97.13 |
| Allowed (%) | 2.87 |
| Outlier (%) | 0.00 |
| Clash score | 8.32 |
| Rotamer outliers (%) | 0.00 |
| Cβ outliers (%) | 0.00 |
| Peptide plane (%) | |
| Cis proline/general | 2.1/0.0 |
| Twisted proline/general | 0.0/0.0 |
| MolProbity score | 1.61 |
| EMRinger score | 2.44 |

REFERENCES

1. C. M. Rudin et al., Treatment of medulloblastoma with hedgehog pathway inhibitor GDC-0449. *N Engl J Med* 361, 1173-1178 (2009).
2. D. D. Von Hoff et al., Inhibition of the hedgehog pathway in advanced basal-cell carcinoma. *N Engl J Med* 361, 1164-1172 (2009).
3. S. A. Brunton et al., Potent agonists of the Hedgehog signaling pathway. *Bioorg Med Chem Lett* 19, 4308-4311 (2009).
4. J. J. Lee et al., Stromal response to Hedgehog signaling restrains pancreatic cancer progression. *Proc Natl Acad Sci USA* 111, E3091-3100 (2014).
5. A. Horn et al., Hedgehog signaling controls fibroblast activation and tissue fibrosis in systemic sclerosis. *Arthritis Rheum* 64, 2724-2733 (2012).
6. F. R. Taylor et al., Enhanced potency of human Sonic hedgehog by hydrophobic modification. *Biochemistry* 40, 4359-4371 (2001).
7. R. K. Mann, P. A. Beachy, Novel lipid modifications of secreted protein signals. *Annu Rev Biochem* 73, 891-923 (2004).
8. J. A. Porter, K. E. Young, P. A. Beachy, Cholesterol modification of hedgehog signaling proteins in animal development. *Science* 274, 255-259 (1996).
9. Z. Chamoun et al., Skinny hedgehog, an acyltransferase required for palmitoylation and activity of the hedgehog signal. *Science* 293, 2080-2084 (2001).
10. D. M. Stone et al., The tumour-suppressor gene patched encodes a candidate receptor for Sonic hedgehog. *Nature* 384, 129-134 (1996).
11. P. W. Ingham, A. M. Taylor, Y. Nakano, Role of the *Drosophila* patched gene in positional signalling. *Nature* 353, 184-187 (1991).
12. Y. Chen, G. Struhl, Dual roles for patched in sequestering and transducing Hedgehog. Cell 87, 553-563 (1996).

13. L. V. Goodrich, L. Milenkovic, K. M. Higgins, M. P. Scott, Altered neural cell fates and medulloblastoma in mouse patched mutants. *Science* 277, 1109-1113 (1997).
14. N. Fuse et al., Sonic hedgehog protein signals not as a hydrolytic enzyme but as an apparent ligand for patched. *Proc Natl Acad Sci USA* 96, 10992-10999 (1999).
15. P. W. Ingham, A. P. McMahon, Hedgehog signaling in animal development: paradigms and principles. *Genes Dev* 15, 3059-3087 (2001).
16. M. K. Cooper et al., A defective response to Hedgehog signaling in disorders of cholesterol biosynthesis. *Nat Genet* 33, 508-513 (2003).
17. B. R. Myers, L. Neahring, Y. Zhang, K. J. Roberts, P. A. Beachy, Rapid, direct activity assays for Smoothened reveal Hedgehog pathway regulation by membrane cholesterol and extracellular sodium. *Proc Natl Acad Sci USA* 114, E11141-E11150 (2017).
18. G. Luchetti et al., Cholesterol activates the G-protein coupled receptor Smoothened to promote Hedgehog signaling. *Elife* 5 (2016).
19. 1. Deshpande et al., Smoothened stimulation by membrane sterols drives Hedgehog pathway activity. *Nature* 571, 284-288 (2019).
20. X. Qi et al., Cryo-EM structure of oxysterol-bound human Smoothened coupled to a heterotrimeric Gi. *Nature* 571, 279-283 (2019).
21. P. Huang et al., Structural Basis of Smoothened Activation in Hedgehog Signaling. *Cell* 174, 312-324 e316 (2018).
22. X. Gong et al., Structural basis for the recognition of Sonic Hedgehog by human Patched1. *Science* 361 (2018).
23. X. Qi, P. Schmiege, E. Coutavas, X. Li, Two Patched molecules engage distinct sites on Hedgehog yielding a signaling-competent complex. *Science* 10.1126/science.aas8843 (2018).
24. Y. Zhang et al., Structural Basis for Cholesterol Transport-like Activity of the Hedgehog Receptor Patched. *Cell* 175, 1352-1364 e1314 (2018).
25. H. Qian et al., Inhibition of tetrameric Patched1 by Sonic Hedgehog through an asymmetric paradigm. *Nat Commun* 10, 2320 (2019).
26. X. Qi, P. Schmiege, E. Coutavas, J. Wang, X. Li, Structures of human Patched and its complex with native palmitoylated sonic hedgehog. *Nature* 560, 128-132 (2018).
27. C. Hamers-Casterman et al., Naturally occurring antibodies devoid of light chains. *Nature* 363, 446-448 (1993).
28. S. Muyldermans, Nanobodies: natural single-domain antibodies. *Annu Rev Biochem* 82, 775-797 (2013).
29. C. McMahon et al., Yeast surface display platform for rapid discovery of conformationally selective nanobodies. *Nat Struct Mol Biol* 25, 289-296 (2018).
30. J. Taipale, M. K. Cooper, T. Maiti, P. A. Beachy, Patched acts catalytically to suppress the activity of Smoothened. *Nature* 418, 892-897 (2002).
31. E. E. Wrenbeck et al., Plasmid-based one-pot saturation mutagenesis. *Nat Methods* 13, 928-930 (2016).
32. R. F. Hwang et al., Inhibition of the hedgehog pathway targets the tumor-associated stroma in pancreatic cancer. *Mol Cancer Res* 10, 1147-1157 (2012).
33. C. Qi, G. Di Minin, I. Vercellino, A. Wutz, V. M. Korkhov, Structural basis of sterol recognition by human hedgehog receptor PTCH1. Science Advances 5 (2019).
34. M. A. Seeger et al., Structural asymmetry of AcrB trimer suggests a peristaltic pump mechanism. *Science* 313, 1295-1298 (2006).
35. S. L. Liu et al., Orthogonal lipid sensors identify transbilayer asymmetry of plasma membrane cholesterol. *Nat Chem Biol* 13, 268-274 (2017).
36. R. D. Paladini, J. Saleh, C. Qian, G. X. Xu, L. L. Rubin, Modulation of hair growth with small molecule agonists of the hedgehog signaling pathway. *J Invest Dermatol* 125, 638-646 (2005).
37. W. J. Lu et al., Neuronal delivery of Hedgehog directs spatial patterning of taste organ regeneration. *Proc Natl Acad Sci USA* 115, E200-E209 (2018).
38. D. Castillo-Azofeifa et al., Sonic hedgehog from both nerves and epithelium is a key trophic factor for taste bud maintenance. *Development* 144, 3054-3065 (2017).
39. K. J. Roberts, A. M. Kershner, P. A. Beachy, The Stromal Niche for Epithelial Stem Cells: A Template for Regeneration and a Brake on Malignancy. *Cancer Cell* 32, 404-410 (2017).
40. M. Gerling et al., Stromal Hedgehog signalling is downregulated in colon cancer and its restoration restrains tumour growth. *Nat Commun* 7, 12321 (2016).
41. A. D. Rhim et al., Stromal elements act to restrain, rather than support, pancreatic ductal adenocarcinoma. *Cancer Cell* 25, 735-747 (2014).
42. K. Shin et al., Hedgehog signaling restrains bladder cancer progression by eliciting stromal production of urothelial differentiation factors. *Cancer Cell* 26, 521-533 (2014).
43. J. J. Lee et al., Control of inflammation by stromal Hedgehog pathway activation restrains colitis. *Proc Natl Acad Sci USA* 113, E7545-E7553 (2016).
44. A. Lim, K. Shin, C. Zhao, S. Kawano, P. A. Beachy, Spatially restricted Hedgehog signalling regulates HGF-induced branching of the adult prostate. *Nat Cell Biol* 16, 1135-1145 (2014).
45. R. Tevlin et al., Pharmacological rescue of diabetic skeletal stem cell niches. *Sci Transl Med* 9 (2017).
46. T. J. Carney, P. W. Ingham, Drugging Hedgehog: signaling the pathway to translation. BMC Bio/11, 37 (2013).
47. M. Zwama, A. Yamaguchi, Molecular mechanisms of AcrB-mediated multidrug export. Res Microbio/169, 372-383 (2018).
48. E. D. Carstea et al., Niemann-Pick C1 disease gene: homology to mediators of cholesterol homeostasis. *Science* 277, 228-231 (1997).
49. A. Noor et al., Disruption at the PTCHD1 Locus on Xp22.11 in Autism spectrum disorder and intellectual disability. *Sci Transl Med* 2, 49ra68 (2010).
50. C. R. Marshall et al., Structural variation of chromosomes in autism spectrum disorder. *Am J Hum Genet* 82, 477-488 (2008).

Example 2

Systemic pathway activation of the Hedgehog pathway may have undesirable effects, and therapeutic application has been difficult for lack of pathway-activating agents that are amenable to tissue targeting. As a single-domain protein, the nanobodies disclosed herein are amenable to engineering and can be targeted to specific tissue compartments for precise control of Hedgehog pathway activity.

Figure 9D:
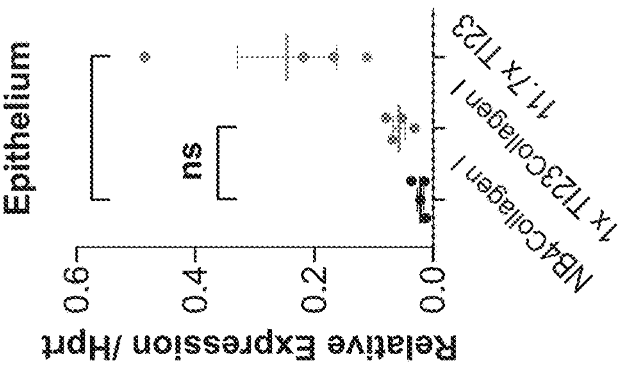
FIG. 9A-9D FIG. 9A: Construct design for TI23Collagen1 (SEQ ID NO:26). SP: Signal Peptide
Figure 9C:
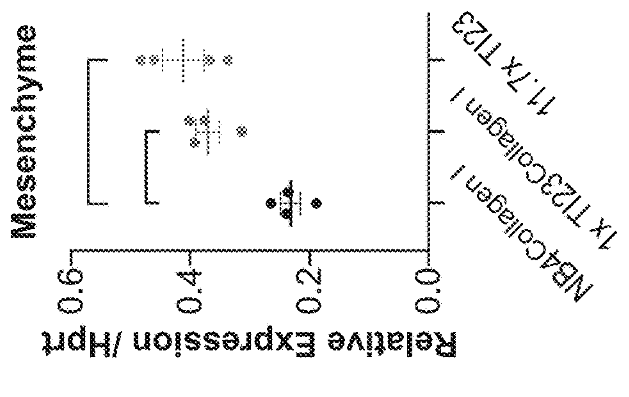
Figure 9A:
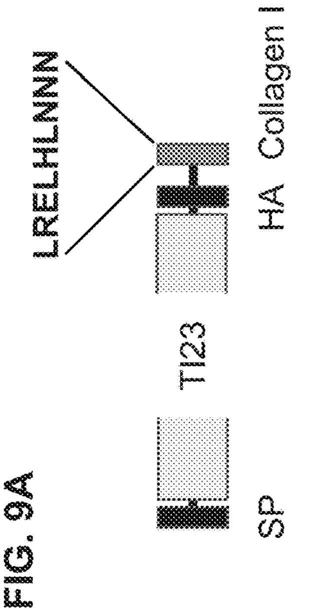
Figure 9B:
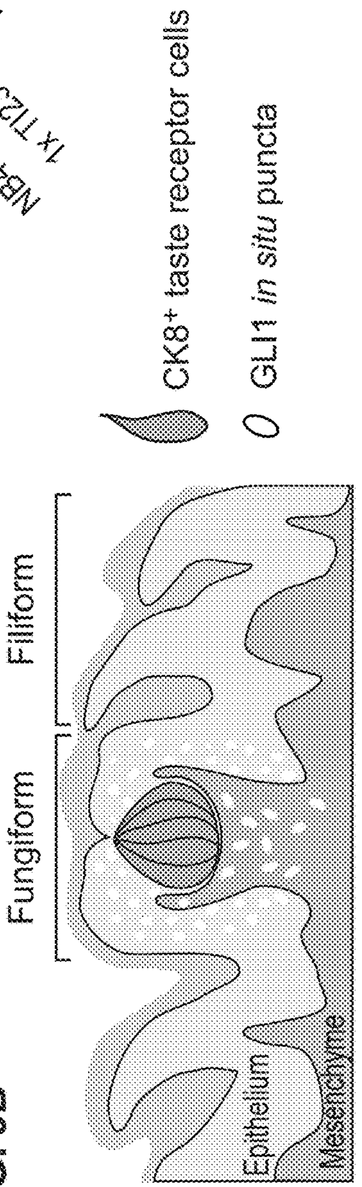
Figure 10:
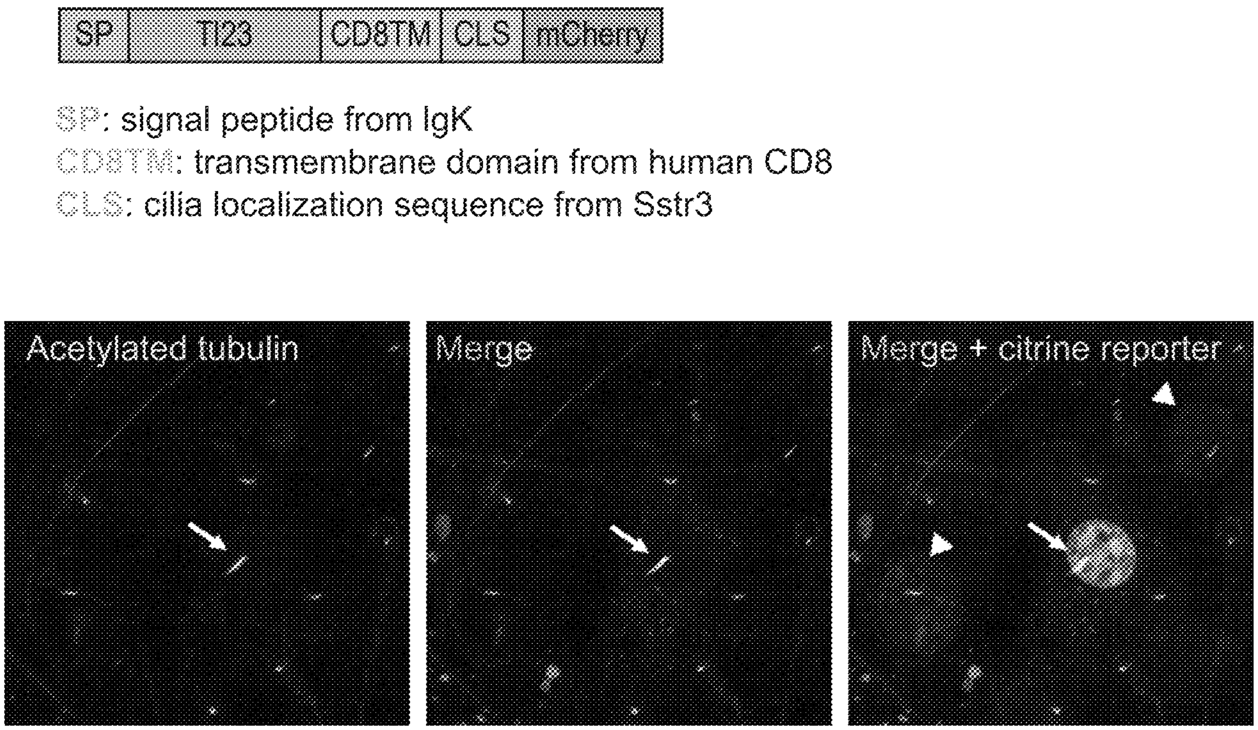
FIG. 10. Top: Design of a ciliary membrane tethered TI23 nanobody. A signal peptide (SP) is fused to the N terminus of the TI23 nanobody for secretory pathway targeting, and the transmembrane domain of CD8 (CD8TM) is used for cell surface display of the nanobody. Cilia targeting is achieved by fusing the cilia localization sequence from Sstr3 to the C terminal of the CD8 transmembrane domain. Bottom: Validation of localization and activity of ciliary membrane tethered TI23. A plasmid encoding the ciliary membrane tethered TI23 was transfected into a Hedgehog pathway activity reporter cell line, which expresses an H2B-citrine reporter under a Gli promoter when pathway is activated. mCherry signal shows cilia localization of TI23, as evidenced by its colocalization with a cilia marker-acetylated tubulin. Citrine reporter is expressed only in the cell expressing TI23 (arrow), but not in adjacent untransfected cells (arrowhead), demonstrating that pathway activation by the ciliary membrane tethered TI23 is cell autonomous. Scale bar, 20 μm.
Figure 11:
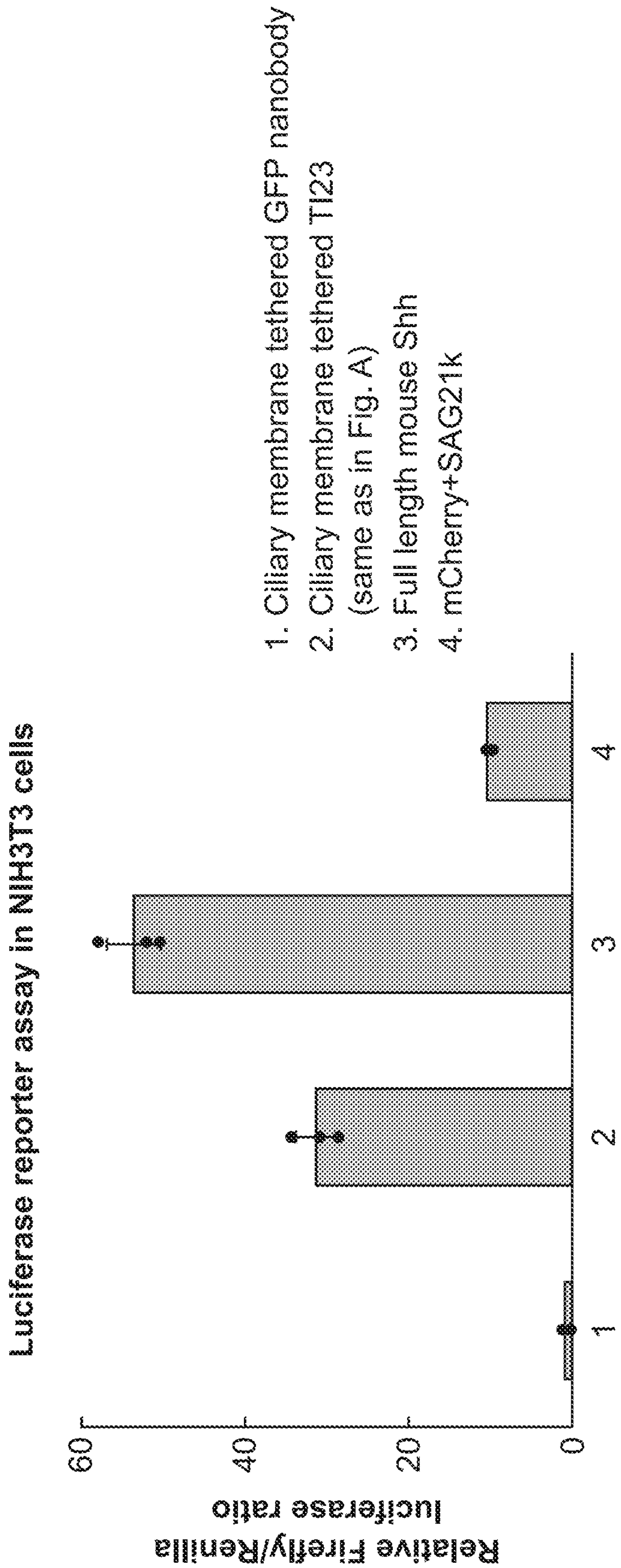
FIG. 11. Validation of pathway activation by the ciliary membrane tethered TI23 using a dual-luciferase reporter assay in NIH 3T3 cells. Constructs 1~4 were separately co-transfected with Gli-Firefly/SV40-*Renilla* luciferase dual-reporter plasmids. The relative ratio of Firefly/*Renilla* luciferase reflects Hedgehog pathway activation. The ciliary membrane tethered TI23 (construct 2) shows robust activation compared to a negative control GFP nanobody (construct 1). SAG21k is a small molecule pathway agonist.

Recent work has brought new light to bear on a role for the mesenchymal niche as a stromal template for epithelial organ maintenance and regeneration through the simultaneous production of proliferative and differentiative cues. To achieve preferential Hedgehog pathway activation in the mesenchymal compartment, we appended a collagen type I binding peptide (SEQ ID NO: 26, LRELHLNNN) to the TI23 sequence and named this variant $TI23^{Collagen\ I}$, or $TI23^{Col1}$ (FIG. 9A). The mature protein is shown in SEQ ID NO:25. As type I collagen is widely expressed in the mesenchymal compartment but not in the epithelium, we expected $TI23^{Col1}$ to concentrate in and efficiently activate the Hedgehog pathway in the mesenchyme. The lingual epithelium can readily be separated from mesenchyme after dispase treatment, and we used tongue to demonstrate tissue targeting (FIG. 9B). In animals receiving the $TI23^{Col1}$ virus, mesenchymal Gli1 expression was observed at a similar level as animals receiving the TI23 virus at a titer around 11.7-fold higher (FIG. 9C). Thus, only ~8.5% the titer of the $TI23^{Col1}$ virus is required as compared to the TI23 virus for a similar level of mesenchymal expression. Note that Gli1 expression in the epithelium, in contrast, is minimal in animals receiving $TI23^{Col1}$ (FIG. 9D), similar to the level in control animals and indicating that $TI23^{Col1}$ preferentially activates the Hedgehog pathway in the mesenchyme.

A similar strategy of fusing a peptide or nanobody or other targeting sequence can be used to restrict Hedgehog pathway activation to other specific compartments.

Example 3

TI23, a fully genetically-encodable Hedgehog protein mimic, also allows for protein engineering of diverse sets of pathway agonists with unprecedented properties. For example, currently no natural or synthetic molecule is capable of inhibiting Patched1 and stimulating Hh pathway activity in a cell autonomous or cell-type specific manner. This can be achieved by engineering a cilia membrane-tethered TI23 (Figure A and B), which inactivates Patched1 on the ciliary membrane specifically within the cell expressing the nanobody, shown in SEQ ID NO:27.

The utility of such an engineered TI23 is several fold: 1. If combined with a cell or tissue type specific promoter, such a construct would provide a promising modality to activate the Hh pathway in genetically defined cell sub-populations. 2. The expression of this cilia membrane tethered TI23 can also be under the control of an inducible promoter that responds to specific chemical or physical (optical, magnetic, acoustic, temperature, etc) stimuli, for controlled pathway activation. 3. In addition, since both the expression level of TI23 and the affinity between the nanobody and Patched1 can be fine-tuned, the extent of Hh pathway activation can be precisely modulated using such an approach.

| Sequences |
|---|
| >10 (SEQ ID NO: 1)<br>QVQLQESGGGLVQAGGSLRLSCAASGTIFLSHYMGWYRQAPGKERELVAAINFGTSTNYADS<br>VKGRFTISRDNAKNTVYLQMNSLKPEDTAVYYCAAAFTPIFHHLYWGQGTQVTVSS |
| >12 (SEQ ID NO: 2)<br>QVQLQESGGGLVQAGGSLRLSCAASGSIFLPYYMGWYRQAPGKERELVASIDQGGNTYYADS<br>VKGRFTISRDNAKNTVYLQMNSLKPEDTAVYYCAVAYTPEVYHIYWGQGTQVTVSS |
| >13 (SEQ ID NO: 3)<br>QVQLQESGGGLVQAGGSLRLSCAASGSISDTGDMGWYRQAPGKERELVASIGGGTSTNYAD<br>SVKGRFTISRDNAKNTVYLQMNSLKPEDTAVYYCAALRNYGIFYVSKYSYWGQGTQVTVSS |
| >15 (SEQ ID NO: 4)<br>QVQLQESGGGLVQAGGSLRLSCAASGNIFDDGNMGWYRQAPGKEREFVAAIAYGSSTNYAD<br>SVKGRFTISRDNAKNTVYLQMNSLKPEDTAVYYCAAYFPDNPPYYYWGQGTQVTVSS |
| >17 (SEQ ID NO: 5)<br>QVQLQESGGGLVQAGGSLRLSCAASGNIFDGNLMGWYRQAPGKEREFVAAITGGASTYYADS<br>VKGRFTISRDNAKNTVYLQMNSLKPEDTAVYYCAAGWLYTPVFYYWGQGTQVTVSS |
| >19 (SEQ ID NO: 6)<br>QVQLQESGGGLVQAGGSLRLSCAASGYIFWYVNMGWYRQAPGKERELVAGIDHGTNTYYAD<br>SVKGRFTISRDNAKNTVYLQMNSLKPEDTAVYYCAAGKGYRYGFQYWGQGTQVTVSS |
| >1 (SEQ ID NO: 7)<br>QVQLQESGGGLVQAGGSLRLSCAASGTIFYLYYMGWYRQAPGKEREFVAGIGEGGTTNYADS<br>VKGRFTISRDNAKNTVYLQMNSLKPEDTAVYYCAAVINVLGHHGYWGQGTQVTVSS |
| >20 (SEQ ID NO: 8)<br>QVQLQESGGGLVQAGGSLRLSCAASGNIFLWESMGWYRQAPGKEREFVASINTGSSTNYADS<br>VKGRFTISRDNAKNTVYLQMNSLKPEDTAVYYCAVRVISWYNFRYWGQGTQVTVSS |
| >22 (SEQ ID NO: 9)<br>QVQLQESGGGLVQAGGSLRLSCAASGTIFQAGGMGWYRQAPGKEREFVATIGHGSSTYYAD<br>SVKGRFTISRDNAKNTVYLQMNSLKPEDTAVYYCAAWWDLRHEYWGQGTQVTVSS |
| >23 (SEQ ID NO: 10)<br>QVQLQESGGGLVQAGGSLRLSCAASGNIFAYYIMGWYRQAPGKERELVAGIDIGGNTNYADSV<br>KGRFTISRDNAKNTVYLQMNSLKPEDTAVYYCAVQAVPYRYHGYWGQGTQVTVSS |

-continued

| Sequences |
|---|
| >2 (SEQ ID NO: 11)<br>QVQLQESGGGLVQAGGSLRLSCAASGTISTATQMGWYRQAPGKEREFVAAIAYGGITYYADS<br>VKGRFTISRDNAKNTVYLQMNSLKPEDTAVYYCAALPDYYHYHVYWGQGTQVTVSS |
| >3 (SEQ ID NO: 12)<br>QVQLQESGGGLVQAGGSLRLSCAASGSISTIQQMGWYRQAPGKEREFVAAIGFGTITYYADSV<br>KGRFTISRDNAKNTVYLQMNSLKPEDTAVYYCAAQWTIWDAHTYWGQGTQVTVSS |
| >6 (SEQ ID NO: 13)<br>QVQLQESGGGLVQAGGSLRLSCAASGYIFADQGMGWYRQAPGKERELVATIDVGATTNYADS<br>VKGRFTISRDNAKNTVYLQMNSLKPEDTAVYYCAVGITINGVIYVPHGYWGQGTQVTVSS |
| >10 (SEQ ID NO: 14)<br>QVQLQESGGGLVQAGGSLRLSCAASGTIFLSHYMGWYRQAPGKERELVAAINFGTSTNYADS<br>VKGRFTISRDNAKNTVYLQMNSLKPEDTAVYYCAAAFTPIFHHLYWGQGTQVTVSS |
| >12 (SEQ ID NO: 15)<br>QVQLQESGGGLVQAGGSLRLSCAASGSIFLPYYMGWYRQAPGKERELVASIDQGGNTYYADS<br>VKGRFTISRDNAKNTVYLQMNSLKPEDTAVYYCAVAYTPEVYHIYWGQGTQVTVSS |
| >13 (SEQ ID NO: 16)<br>QVQLQESGGGLVQAGGSLRLSCAASGSISDTGDMGWYRQAPGKERELVASIGGGTSTNYAD<br>SVKGRFTISRDNAKNTVYLQMNSLKPEDTAVYYCAALRNYGIFYVSKYSYWGQGTQVTVSS |
| >17 (SEQ ID NO: 17)<br>QVQLQESGGGLVQAGGSLRLSCAASGNIFDGNLMGWYRQAPGKEREFVAAITGGASTYYADS<br>VKGRFTISRDNAKNTVYLQMNSLKPEDTAVYYCAAGWLYTPVFYYWGQGTQVTVSS |
| Known sequence variations of SEQ ID NO. 10<br>Variations of SEQ NO. 10 have been observed that maintain or outperform SEQ NO: 10 in activity. Some key positions in the sequence that affect the activity are summarized as follows.<br>(SEQ ID NO: 24)<br>QVQLQESGGGLVQAGGSLRLSCAASGNIFAYYIMGWYRQAPGKERELVA[G/A/S/T/D]IDI<br>GGNTNYADSVKGRFTISRDNAKN[T/N]VYLQMNSLKPEDTAVYYCAVQAVP[Y/I]RY[H/<br>R][G/R]YWGQGTQVTVSS |
| Nanobody sequences include:<br>>10-1 (SEQ ID NO. 18)<br>QVQLQESGGGLVQAGGSLRLSCAASGNIFAYYIMGWYRQAPGKERELVAGIDIGGNTNYA<br>DSVKGRFTISRDNAKNTVYLQMNSLKPEDTAVYYCAVQAVPYRYHRYWGQGTQVTVSS |
| >10-2 (SEQ ID NO. 19)<br>QVQLQESGGGLVQAGGSLRLSCAASGNIFAYYIMGWYRQAPGKERELVASIDIGGSTNYA<br>DSVKGRFTISRDNAKNTVYLQMNSLKPEDTAVYHCVVQAVPYRYRGYWGQGTQVTVSS |
| >10-3 (SEQ ID NO. 20)<br>QVQLQESGGGLVQAGGSLRLSCAASGNIFAYYIMGWYRQAPGKERELVAAIDIGGNTNYA<br>DSVKGRFTVSRDNAKNTVYLQMNSLKPEDTAVYYGAVQAVPYRYHRYWGQGTQVTVSS |
| >10-4 (SEQ ID NO. 21)<br>QVQLQESGGGLVQAGGSLRLSCAASGNIFAYYIMGWYRQAPGKERELVADIDIGGNTNYA<br>DSVKGRFTISRDNTKNNVYLQMNSLKPEDTAVYYCAVQAVPYRYHGYWGQGTQVTVSS |
| >10-5 (SEQ ID NO. 22)<br>QVQLQESGGGLVQAGGNLRLSCAASGNIFAYYIMGWYRQAPGKERELVATIDIGSNTNYA<br>DSVKGRFNISRDNAKNIVYLQMNSLKPEDTAVYYCAVQAVPYRYRRYWGQGTQVTVSS |
| >10-6 (SEQ ID NO. 23)<br>QVQLQESGGGLVQAGGSLRLSCAASGNIFAYYIMGWYRQAPGKERELVATIDIGGNTNYA<br>DSVKGRFTISRDNAKNNVYLQMNSLKPEDTAVYYCAVQAVPIRYRRYWGQGTQVTVSS |
| SEQ ID NO: 25, TI23$^{Col1}$ protein, comprising the COL1 binding sequence (SEQ ID NO: 25) fused to the terminus through a linker.<br>QVQLQESGGGLVQAGGSLRLSCAASGNIFAYYIMGWYRQAPGKERELVATIDIGGNTNYADSV<br>KGRFTISRDNAKNNVYLQMNSLKPEDTAVYYCAVQAVPIRYRRYWGQGTQVTVSSYPYDVPD<br>YAGSGLRELHLNNN |
| SEQ ID NO: 26<br>LRELHLNNN |
| SEQ ID NO: 27, mature TI23 nanobody is fused to the transmembrane domain of CD8 (SEQ ID NO: 27) and a cilia localization sequence (SEQ ID NO: 28):<br>QVQLQESGGGLVQAGGSLRLSCAASGNIFAYYIMGWYRQAPGKERELVATIDIGGNTNYADSV<br>KGRFTISRDNAKNNVYLQMNSLKPEDTAVYYCAVQAVPIRYRRYWGQGTQVTVSSGSQFRVS<br>PLDRTWNLGETVELKCQVLLSNPTSGCSWLFQPRGAAASPTFLLYLSQNKPKAAEGLDTQRFS |

-continued

| Sequences |
|---|
| GKRLGDTFVLTLSDFRRENEGYYFCSALSNSIMYFSHFVPVFLPAKPTTTPAPRPPTPAPTIASQ<br>PLSLRPEACRPAAGGAVHTRGLDFACDIYIWAPLAGTCGVLLLSLVITLYCLSYRFKQGFRRILL<br>RPSRRIRSQEPGSGPPEKTEEEEDEEEEERREEEERRMQRGQEMNGRLSQIAQAGTSGQQP<br>RPCTGTAKEQQLLPQEATAGDKASTLSHL |
| SEQ ID NO: 28 CD8a transmembrane domain<br>SQFRVSPLDRTWNLGETVELKCQVLLSNPTSGCSWLFQPRGAAASPTFLLYLSQNKPKAAEGL<br>DTQRFSGKRLGDTFVLTLSDFRRENEGYYFCSALSNSIMYFSHFVPVFLPAKPTTTPAPRPPTP<br>APTIASQPLSLRPEACRPAAGGAVHTRGLDFACDIYIWAPLAGTCGVLLLSLVITLYC |
| SEQ ID NO: 29 cilia localization sequence, Sstr3 CLS (aa 325-428<br>from the original protein)<br>LSYRFKQGFRRILLRPSRRIRSQEPGSGPPEKTEEEEDEEEEERREEEERRMQRGQEMNGRL<br>SQIAQAGTSGQQPRPCTGTAKEQQLLPQEATAGDKASTLSHL |

What is claimed is:

1. A polypeptide comprising an antigen-binding domain (ABD) that preferentially binds to human Patched 1 (PTCH1) and which activates the Hedgehog signaling pathway, wherein the ABD comprises SEQ ID NO:10.

2. A pharmaceutical formulation comprising a polypeptide of claim 1, and a pharmaceutically acceptable excipient.

3. The pharmaceutical formulation of claim 2 in a unit dose form.

4. A polypeptide comprising an antigen-binding domain (ABD) that preferentially binds to human Patched 1 (PTCH1), and which activates the Hedgehog signaling pathway, comprising SEQ ID NO:23.

5. The polypeptide of claim 4, joined to a human Fc polypeptide.

6. The polypeptide of claim 4, joined to a targeting moiety.

7. The polypeptide of claim 6, wherein the targeting moiety comprises a cilia localization polypeptide of SEQ ID NO:29 and a transmembrane domain, optionally joined through a peptide linker.

8. The polypeptide of claim 6, wherein the targeting moiety comprises a collagen binding polypeptide of SEQ ID NO:26, optionally joined through a peptide linker.

* * * * *

SEQUENCE LISTING

```
<160> NUMBER OF SEQ ID NOS: 49

<210> SEQ ID NO 1
<211> LENGTH: 118
<212> TYPE: PRT
<213> ORGANISM: Artificial sequence
<220> FEATURE:
<223> OTHER INFORMATION: synthetic sequence

<400> SEQUENCE: 1

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Leu Ser His
            20                  25                  30

Tyr Met Gly Trp Tyr Arg Gln Ala Pro Gly Lys Glu Arg Glu Leu Val
        35                  40                  45

Ala Ala Ile Asn Phe Gly Thr Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ala Phe Thr Pro Ile Phe His His Leu Tyr Trp Gly Gln Gly Thr
            100                 105                 110

Gln Val Thr Val Ser Ser
        115


<210> SEQ ID NO 2
<211> LENGTH: 118
<212> TYPE: PRT
<213> ORGANISM: Artificial sequence
<220> FEATURE:
<223> OTHER INFORMATION: synthetic sequence

<400> SEQUENCE: 2

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Leu Pro Tyr
            20                  25                  30

Tyr Met Gly Trp Tyr Arg Gln Ala Pro Gly Lys Glu Arg Glu Leu Val
        35                  40                  45

Ala Ser Ile Asp Gln Gly Gly Asn Thr Tyr Tyr Ala Asp Ser Val Lys
    50                  55                  60
```

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Val Ala Tyr Thr Pro Glu Val Tyr His Ile Tyr Trp Gly Gln Gly Thr
100 105 110

Gln Val Thr Val Ser Ser
115

<210> SEQ ID NO 3
<211> LENGTH: 122
<212> TYPE: PRT
<213> ORGANISM: Artificial sequence
<220> FEATURE:
<223> OTHER INFORMATION: synthetic sequence

<400> SEQUENCE: 3

Gln Val Gln Leu Gln Glu Ser Gly Gly Gly Leu Val Gln Ala Gly Gly
1 5 10 15

Ser Leu Arg Leu Ser Cys Ala Ala Ser Gly Ser Ile Ser Asp Thr Gly
20 25 30

Asp Met Gly Trp Tyr Arg Gln Ala Pro Gly Lys Glu Arg Glu Leu Val
35 40 45

Ala Ser Ile Gly Gly Gly Thr Ser Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Ala Leu Arg Asn Tyr Gly Ile Phe Tyr Val Ser Lys Tyr Ser Tyr Trp
100 105 110

Gly Gln Gly Thr Gln Val Thr Val Ser Ser
115 120

<210> SEQ ID NO 4
<211> LENGTH: 118
<212> TYPE: PRT
<213> ORGANISM: Artificial sequence
<220> FEATURE:
<223> OTHER INFORMATION: synthetic sequence

<400> SEQUENCE: 4

Gln Val Gln Leu Gln Glu Ser Gly Gly Gly Leu Val Gln Ala Gly Gly
1 5 10 15

Ser Leu Arg Leu Ser Cys Ala Ala Ser Gly Asn Ile Phe Asp Asp Gly
20 25 30

Asn Met Gly Trp Tyr Arg Gln Ala Pro Gly Lys Glu Arg Glu Phe Val
35 40 45

Ala Ala Ile Ala Tyr Gly Ser Ser Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Ala Tyr Phe Pro Asp Asn Pro Pro Tyr Tyr Tyr Trp Gly Gln Gly Thr
100 105 110

Gln Val Thr Val Ser Ser

```
        115


<210> SEQ ID NO 5
<211> LENGTH: 118
<212> TYPE: PRT
<213> ORGANISM: Artificial sequence
<220> FEATURE:
<223> OTHER INFORMATION: synthetic sequence

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Asp Gly Asn
            20                  25                  30

Leu Met Gly Trp Tyr Arg Gln Ala Pro Gly Lys Glu Arg Glu Phe Val
        35                  40                  45

Ala Ala Ile Thr Gly Gly Ala Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Gly Trp Leu Tyr Thr Pro Val Phe Tyr Tyr Trp Gly Gln Gly Thr
            100                 105                 110

Gln Val Thr Val Ser Ser
        115


<210> SEQ ID NO 6
<211> LENGTH: 118
<212> TYPE: PRT
<213> ORGANISM: Artificial sequence
<220> FEATURE:
<223> OTHER INFORMATION: synthetic sequence

<400> SEQUENCE: 6

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Phe Trp Tyr Val
            20                  25                  30

Asn Met Gly Trp Tyr Arg Gln Ala Pro Gly Lys Glu Arg Glu Leu Val
        35                  40                  45

Ala Gly Ile Asp His Gly Thr Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Gly Lys Gly Tyr Arg Tyr Gly Phe Gln Tyr Trp Gly Gln Gly Thr
            100                 105                 110

Gln Val Thr Val Ser Ser
        115


<210> SEQ ID NO 7
<211> LENGTH: 118
<212> TYPE: PRT
<213> ORGANISM: Artificial sequence
<220> FEATURE:
<223> OTHER INFORMATION: synthetic sequence

<400> SEQUENCE: 7
```

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Tyr Leu Tyr
            20                  25                  30

Tyr Met Gly Trp Tyr Arg Gln Ala Pro Gly Lys Glu Arg Glu Phe Val
        35                  40                  45

Ala Gly Ile Gly Glu Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Val Ile Asn Val Leu Gly His His Gly Tyr Trp Gly Gln Gly Thr
            100                 105                 110

Gln Val Thr Val Ser Ser
        115
```

<210> SEQ ID NO 8
<211> LENGTH: 118
<212> TYPE: PRT
<213> ORGANISM: Artificial sequence
<220> FEATURE:
<223> OTHER INFORMATION: synthetic sequence

<400> SEQUENCE: 8

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Leu Trp Glu
            20                  25                  30

Ser Met Gly Trp Tyr Arg Gln Ala Pro Gly Lys Glu Arg Glu Phe Val
        35                  40                  45

Ala Ser Ile Asn Thr Gly Ser Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Arg Val Ile Ser Trp Tyr Asn Phe Arg Tyr Trp Gly Gln Gly Thr
            100                 105                 110

Gln Val Thr Val Ser Ser
        115
```

<210> SEQ ID NO 9
<211> LENGTH: 116
<212> TYPE: PRT
<213> ORGANISM: Artificial sequence
<220> FEATURE:
<223> OTHER INFORMATION: synthetic sequence

<400> SEQUENCE: 9

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Ala Gly
            20                  25                  30

Gly Met Gly Trp Tyr Arg Gln Ala Pro Gly Lys Glu Arg Glu Phe Val
        35                  40                  45

Ala Thr Ile Gly His Gly Ser Ser Thr Tyr Tyr Ala Asp Ser Val Lys
```

```
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Trp Trp Asp Leu Arg His Glu Tyr Trp Gly Gln Gly Thr Gln Val
            100                 105                 110

Thr Val Ser Ser
        115


<210> SEQ ID NO 10
<211> LENGTH: 118
<212> TYPE: PRT
<213> ORGANISM: Artificial sequence
<220> FEATURE:
<223> OTHER INFORMATION: synthetic sequence

<400> SEQUENCE: 10

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Ala Tyr Tyr
            20                  25                  30

Ile Met Gly Trp Tyr Arg Gln Ala Pro Gly Lys Glu Arg Glu Leu Val
        35                  40                  45

Ala Gly Ile Asp Ile Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gln Ala Val Pro Tyr Arg Tyr His Gly Tyr Trp Gly Gln Gly Thr
            100                 105                 110

Gln Val Thr Val Ser Ser
        115


<210> SEQ ID NO 11
<211> LENGTH: 118
<212> TYPE: PRT
<213> ORGANISM: Artificial sequence
<220> FEATURE:
<223> OTHER INFORMATION: synthetic sequence

<400> SEQUENCE: 11

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Thr Ala Thr
            20                  25                  30

Gln Met Gly Trp Tyr Arg Gln Ala Pro Gly Lys Glu Arg Glu Phe Val
        35                  40                  45

Ala Ala Ile Ala Tyr Gly Gly Ile Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Leu Pro Asp Tyr Tyr His Tyr His Val Tyr Trp Gly Gln Gly Thr
            100                 105                 110
```

```
Gln Val Thr Val Ser Ser
        115


<210> SEQ ID NO 12
<211> LENGTH: 118
<212> TYPE: PRT
<213> ORGANISM: Artificial sequence
<220> FEATURE:
<223> OTHER INFORMATION: synthetic sequence

<400> SEQUENCE: 12

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ser Thr Ile Gln
            20                  25                  30

Gln Met Gly Trp Tyr Arg Gln Ala Pro Gly Lys Glu Arg Glu Phe Val
        35                  40                  45

Ala Ala Ile Gly Phe Gly Thr Ile Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Gln Trp Thr Ile Trp Asp Ala His Thr Tyr Trp Gly Gln Gly Thr
            100                 105                 110

Gln Val Thr Val Ser Ser
        115


<210> SEQ ID NO 13
<211> LENGTH: 122
<212> TYPE: PRT
<213> ORGANISM: Artificial sequence
<220> FEATURE:
<223> OTHER INFORMATION: synthetic sequence

<400> SEQUENCE: 13

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Phe Ala Asp Gln
            20                  25                  30

Gly Met Gly Trp Tyr Arg Gln Ala Pro Gly Lys Glu Arg Glu Leu Val
        35                  40                  45

Ala Thr Ile Asp Val Gly Ala Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gly Ile Thr Ile Asn Gly Val Ile Tyr Val Pro His Gly Tyr Trp
            100                 105                 110

Gly Gln Gly Thr Gln Val Thr Val Ser Ser
        115                 120


<210> SEQ ID NO 14
<211> LENGTH: 118
<212> TYPE: PRT
<213> ORGANISM: Artificial sequence
<220> FEATURE:
<223> OTHER INFORMATION: synthetic sequence
```

<400> SEQUENCE: 14

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Leu Ser His
            20                  25                  30

Tyr Met Gly Trp Tyr Arg Gln Ala Pro Gly Lys Glu Arg Glu Leu Val
        35                  40                  45

Ala Ala Ile Asn Phe Gly Thr Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ala Phe Thr Pro Ile Phe His His Leu Tyr Trp Gly Gln Gly Thr
            100                 105                 110

Gln Val Thr Val Ser Ser
        115
```

<210> SEQ ID NO 15
<211> LENGTH: 118
<212> TYPE: PRT
<213> ORGANISM: Artificial sequence
<220> FEATURE:
<223> OTHER INFORMATION: synthetic sequence

<400> SEQUENCE: 15

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Leu Pro Tyr
            20                  25                  30

Tyr Met Gly Trp Tyr Arg Gln Ala Pro Gly Lys Glu Arg Glu Leu Val
        35                  40                  45

Ala Ser Ile Asp Gln Gly Gly Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Ala Tyr Thr Pro Glu Val Tyr His Ile Tyr Trp Gly Gln Gly Thr
            100                 105                 110

Gln Val Thr Val Ser Ser
        115
```

<210> SEQ ID NO 16
<211> LENGTH: 122
<212> TYPE: PRT
<213> ORGANISM: Artificial sequence
<220> FEATURE:
<223> OTHER INFORMATION: synthetic sequence

<400> SEQUENCE: 16

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ser Asp Thr Gly
            20                  25                  30

Asp Met Gly Trp Tyr Arg Gln Ala Pro Gly Lys Glu Arg Glu Leu Val
        35                  40                  45
```

Ala Ser Ile Gly Gly Gly Thr Ser Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Ala Leu Arg Asn Tyr Gly Ile Phe Tyr Val Ser Lys Tyr Ser Tyr Trp
100 105 110

Gly Gln Gly Thr Gln Val Thr Val Ser Ser
115 120

<210> SEQ ID NO 17
<211> LENGTH: 118
<212> TYPE: PRT
<213> ORGANISM: Artificial sequence
<220> FEATURE:
<223> OTHER INFORMATION: synthetic sequence

<400> SEQUENCE: 17

Gln Val Gln Leu Gln Glu Ser Gly Gly Gly Leu Val Gln Ala Gly Gly
1 5 10 15

Ser Leu Arg Leu Ser Cys Ala Ala Ser Gly Asn Ile Phe Asp Gly Asn
20 25 30

Leu Met Gly Trp Tyr Arg Gln Ala Pro Gly Lys Glu Arg Glu Phe Val
35 40 45

Ala Ala Ile Thr Gly Gly Ala Ser Thr Tyr Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Ala Gly Trp Leu Tyr Thr Pro Val Phe Tyr Tyr Trp Gly Gln Gly Thr
100 105 110

Gln Val Thr Val Ser Ser
115

<210> SEQ ID NO 18
<211> LENGTH: 118
<212> TYPE: PRT
<213> ORGANISM: Artificial sequence
<220> FEATURE:
<223> OTHER INFORMATION: synthetic sequence

<400> SEQUENCE: 18

Gln Val Gln Leu Gln Glu Ser Gly Gly Gly Leu Val Gln Ala Gly Gly
1 5 10 15

Ser Leu Arg Leu Ser Cys Ala Ala Ser Gly Asn Ile Phe Ala Tyr Tyr
20 25 30

Ile Met Gly Trp Tyr Arg Gln Ala Pro Gly Lys Glu Arg Glu Leu Val
35 40 45

Ala Gly Ile Asp Ile Gly Gly Asn Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Val Gln Ala Val Pro Tyr Arg Tyr His Arg Tyr Trp Gly Gln Gly Thr
100 105 110

```
Gln Val Thr Val Ser Ser
        115


<210> SEQ ID NO 19
<211> LENGTH: 118
<212> TYPE: PRT
<213> ORGANISM: Artificial sequence
<220> FEATURE:
<223> OTHER INFORMATION: synthetic sequence

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Ala Tyr Tyr
            20                  25                  30

Ile Met Gly Trp Tyr Arg Gln Ala Pro Gly Lys Glu Arg Glu Leu Val
        35                  40                  45

Ala Ser Ile Asp Ile Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr His Cys Val
                85                  90                  95

Val Gln Ala Val Pro Tyr Arg Tyr Arg Gly Tyr Trp Gly Gln Gly Thr
            100                 105                 110

Gln Val Thr Val Ser Ser
        115


<210> SEQ ID NO 20
<211> LENGTH: 118
<212> TYPE: PRT
<213> ORGANISM: Artificial sequence
<220> FEATURE:
<223> OTHER INFORMATION: synthetic sequence

<400> SEQUENCE: 20

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Ala Tyr Tyr
            20                  25                  30

Ile Met Gly Trp Tyr Arg Gln Ala Pro Gly Lys Glu Arg Glu Leu Val
        35                  40                  45

Ala Ala Ile Asp Ile Gly Gly Asn Thr Asn Tyr Ala Asp Ser Val Lys
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Gly Ala
                85                  90                  95

Val Gln Ala Val Pro Tyr Arg Tyr His Arg Tyr Trp Gly Gln Gly Thr
            100                 105                 110

Gln Val Thr Val Ser Ser
        115


<210> SEQ ID NO 21
<211> LENGTH: 118
<212> TYPE: PRT
<213> ORGANISM: Artificial sequence
<220> FEATURE:
<223> OTHER INFORMATION: synthetic sequence
```

<400> SEQUENCE: 21

Gln Val Gln Leu Gln Glu Ser Gly Gly Gly Leu Val Gln Ala Gly Gly
1 5 10 15

Ser Leu Arg Leu Ser Cys Ala Ala Ser Gly Asn Ile Phe Ala Tyr Tyr
20 25 30

Ile Met Gly Trp Tyr Arg Gln Ala Pro Gly Lys Glu Arg Glu Leu Val
35 40 45

Ala Asp Ile Asp Ile Gly Gly Asn Thr Asn Tyr Ala Asp Ser Val Lys
50 55 60

Gly Arg Phe Thr Ile Ser Arg Asp Asn Thr Lys Asn Asn Val Tyr Leu
65 70 75 80

Gln Met Asn Ser Leu Lys Pro Glu Asp Thr Ala Val Tyr Tyr Cys Ala
85 90 95

Val Gln Ala Val Pro Tyr Arg Tyr His Gly Tyr Trp Gly Gln Gly Thr
100 105 110

Gln Val Thr Val Ser Ser
115

<210> SEQ ID NO 22
<211> LENGTH: 118
<212> TYPE: PRT
<213> ORGANISM: Artificial sequence
<220> FEATURE:
<223> OTHER INFORMATION: synthetic sequence

<400> SEQUENCE: 22

Gln Val Gln Leu Gln Glu Ser Gly Gly Gly Leu Val Gln Ala Gly Gly
1 5 10 15

Asn Leu Arg Leu Ser Cys Ala Ala Ser Gly Asn Ile Phe Ala Tyr Tyr
20 25 30

Ile Met Gly Trp Tyr Arg Gln Ala Pro Gly Lys Glu Arg Glu Leu Val
35 40 45

Ala Thr Ile Asp Ile Gly Ser Asn Thr Asn Tyr Ala Asp Ser Val Lys
50 55 60

Gly Arg Phe Asn Ile Ser Arg Asp Asn Ala Lys Asn Ile Val Tyr Leu
65 70 75 80

Gln Met Asn Ser Leu Lys Pro Glu Asp Thr Ala Val Tyr Tyr Cys Ala
85 90 95

Val Gln Ala Val Pro Tyr Arg Tyr Arg Arg Tyr Trp Gly Gln Gly Thr
100 105 110

Gln Val Thr Val Ser Ser
115

<210> SEQ ID NO 23
<211> LENGTH: 118
<212> TYPE: PRT
<213> ORGANISM: Artificial sequence
<220> FEATURE:
<223> OTHER INFORMATION: synthetic sequence

<400> SEQUENCE: 23

Gln Val Gln Leu Gln Glu Ser Gly Gly Gly Leu Val Gln Ala Gly Gly
1 5 10 15

Ser Leu Arg Leu Ser Cys Ala Ala Ser Gly Asn Ile Phe Ala Tyr Tyr
20 25 30

Ile Met Gly Trp Tyr Arg Gln Ala Pro Gly Lys Glu Arg Glu Leu Val
35 40 45

```
Ala Thr Ile Asp Ile Gly Gly Asn Thr Asn Tyr Ala Asp Ser Val Lys
    50                  55                  60

Gly Arg Phe Thr Ile Ser Arg Asp Asn Ala Lys Asn Asn Val Tyr Leu
65                  70                  75                  80

Gln Met Asn Ser Leu Lys Pro Glu Asp Thr Ala Val Tyr Tyr Cys Ala
                85                  90                  95

Val Gln Ala Val Pro Ile Arg Tyr Arg Arg Tyr Trp Gly Gln Gly Thr
            100                 105                 110

Gln Val Thr Val Ser Ser
        115


<210> SEQ ID NO 24
<211> LENGTH: 118
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (50)..(50)
<223> OTHER INFORMATION: The amino acid at position 50 is Gly, Ala, Ser,
      Thr or Asp
<220> FEATURE:
<221> NAME/KEY: SITE
<222> LOCATION: (77)..(77)
<223> OTHER INFORMATION: The amino acid at position 77 is Thr or Asn
<220> FEATURE:
<221> NAME/KEY: SITE
<222> LOCATION: (102)..(102)
<223> OTHER INFORMATION: The amino acid at position 102 is Tyr or Ile
<220> FEATURE:
<221> NAME/KEY: SITE
<222> LOCATION: (105)..(105)
<223> OTHER INFORMATION: The amino acid at position 105 is His or Arg
<220> FEATURE:
<221> NAME/KEY: SITE
<222> LOCATION: (106)..(106)
<223> OTHER INFORMATION: The amino acid at position 106 is Gly or Arg

<400> SEQUENCE: 24

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Ala Tyr Tyr
            20                  25                  30

Ile Met Gly Trp Tyr Arg Gln Ala Pro Gly Lys Glu Arg Glu Leu Val
        35                  40                  45

Ala Xaa Ile Asp Ile Gly Gly Asn Thr Asn Tyr Ala Asp Ser Val Lys
    50                  55                  60

Gly Arg Phe Thr Ile Ser Arg Asp Asn Ala Lys Asn Xaa Val Tyr Leu
65                  70                  75                  80

Gln Met Asn Ser Leu Lys Pro Glu Asp Thr Ala Val Tyr Tyr Cys Ala
                85                  90                  95

Val Gln Ala Val Pro Xaa Arg Tyr Xaa Xaa Tyr Trp Gly Gln Gly Thr
            100                 105                 110

Gln Val Thr Val Ser Ser
        115


<210> SEQ ID NO 25
<211> LENGTH: 139
<212> TYPE: PRT
<213> ORGANISM: Artificial sequence
<220> FEATURE:
<223> OTHER INFORMATION: synthetic sequence
```

<400> SEQUENCE: 25

Gln Val Gln Leu Gln Glu Ser Gly Gly Gly Leu Val Gln Ala Gly Gly
1 5 10 15

Ser Leu Arg Leu Ser Cys Ala Ala Ser Gly Asn Ile Phe Ala Tyr Tyr
20 25 30

Ile Met Gly Trp Tyr Arg Gln Ala Pro Gly Lys Glu Arg Glu Leu Val
35 40 45

Ala Thr Ile Asp Ile Gly Gly Asn Thr Asn Tyr Ala Asp Ser Val Lys
50 55 60

Gly Arg Phe Thr Ile Ser Arg Asp Asn Ala Lys Asn Asn Val Tyr Leu
65 70 75 80

Gln Met Asn Ser Leu Lys Pro Glu Asp Thr Ala Val Tyr Tyr Cys Ala
85 90 95

Val Gln Ala Val Pro Ile Arg Tyr Arg Arg Tyr Trp Gly Gln Gly Thr
100 105 110

Gln Val Thr Val Ser Ser Tyr Pro Tyr Asp Val Pro Asp Tyr Ala Gly
115 120 125

Ser Gly Leu Arg Glu Leu His Leu Asn Asn Asn
130 135

<210> SEQ ID NO 26
<211> LENGTH: 9
<212> TYPE: PRT
<213> ORGANISM: Artificial sequence
<220> FEATURE:
<223> OTHER INFORMATION: synthetic sequence

<400> SEQUENCE: 26

Leu Arg Glu Leu His Leu Asn Asn Asn
1 5

<210> SEQ ID NO 27
<211> LENGTH: 408
<212> TYPE: PRT
<213> ORGANISM: Artificial sequence
<220> FEATURE:
<223> OTHER INFORMATION: synthetic sequence

<400> SEQUENCE: 27

Gln Val Gln Leu Gln Glu Ser Gly Gly Gly Leu Val Gln Ala Gly Gly
1 5 10 15

Ser Leu Arg Leu Ser Cys Ala Ala Ser Gly Asn Ile Phe Ala Tyr Tyr
20 25 30

Ile Met Gly Trp Tyr Arg Gln Ala Pro Gly Lys Glu Arg Glu Leu Val
35 40 45

Ala Thr Ile Asp Ile Gly Gly Asn Thr Asn Tyr Ala Asp Ser Val Lys
50 55 60

Gly Arg Phe Thr Ile Ser Arg Asp Asn Ala Lys Asn Asn Val Tyr Leu
65 70 75 80

Gln Met Asn Ser Leu Lys Pro Glu Asp Thr Ala Val Tyr Tyr Cys Ala
85 90 95

Val Gln Ala Val Pro Ile Arg Tyr Arg Arg Tyr Trp Gly Gln Gly Thr
100 105 110

Gln Val Thr Val Ser Ser Gly Ser Gln Phe Arg Val Ser Pro Leu Asp
115 120 125

Arg Thr Trp Asn Leu Gly Glu Thr Val Glu Leu Lys Cys Gln Val Leu
130 135 140

Leu Ser Asn Pro Thr Ser Gly Cys Ser Trp Leu Phe Gln Pro Arg Gly
145 150 155 160

Ala Ala Ala Ser Pro Thr Phe Leu Leu Tyr Leu Ser Gln Asn Lys Pro
165 170 175

Lys Ala Ala Glu Gly Leu Asp Thr Gln Arg Phe Ser Gly Lys Arg Leu
180 185 190

Gly Asp Thr Phe Val Leu Thr Leu Ser Asp Phe Arg Arg Glu Asn Glu
195 200 205

Gly Tyr Tyr Phe Cys Ser Ala Leu Ser Asn Ser Ile Met Tyr Phe Ser
210 215 220

His Phe Val Pro Val Phe Leu Pro Ala Lys Pro Thr Thr Thr Pro Ala
225 230 235 240

Pro Arg Pro Pro Thr Pro Ala Pro Thr Ile Ala Ser Gln Pro Leu Ser
245 250 255

Leu Arg Pro Glu Ala Cys Arg Pro Ala Ala Gly Gly Ala Val His Thr
260 265 270

Arg Gly Leu Asp Phe Ala Cys Asp Ile Tyr Ile Trp Ala Pro Leu Ala
275 280 285

Gly Thr Cys Gly Val Leu Leu Leu Ser Leu Val Ile Thr Leu Tyr Cys
290 295 300

Leu Ser Tyr Arg Phe Lys Gln Gly Phe Arg Arg Ile Leu Leu Arg Pro
305 310 315 320

Ser Arg Arg Ile Arg Ser Gln Glu Pro Gly Ser Gly Pro Pro Glu Lys
325 330 335

Thr Glu Glu Glu Glu Asp Glu Glu Glu Glu Glu Arg Arg Glu Glu Glu
340 345 350

Glu Arg Arg Met Gln Arg Gly Gln Glu Met Asn Gly Arg Leu Ser Gln
355 360 365

Ile Ala Gln Ala Gly Thr Ser Gly Gln Gln Pro Arg Pro Cys Thr Gly
370 375 380

Thr Ala Lys Glu Gln Gln Leu Leu Pro Gln Glu Ala Thr Ala Gly Asp
385 390 395 400

Lys Ala Ser Thr Leu Ser His Leu
405

<210> SEQ ID NO 28
<211> LENGTH: 185
<212> TYPE: PRT
<213> ORGANISM: Artificial sequence
<220> FEATURE:
<223> OTHER INFORMATION: synthetic sequence

<400> SEQUENCE: 28

Ser Gln Phe Arg Val Ser Pro Leu Asp Arg Thr Trp Asn Leu Gly Glu
1 5 10 15

Thr Val Glu Leu Lys Cys Gln Val Leu Leu Ser Asn Pro Thr Ser Gly
20 25 30

Cys Ser Trp Leu Phe Gln Pro Arg Gly Ala Ala Ala Ser Pro Thr Phe
35 40 45

Leu Leu Tyr Leu Ser Gln Asn Lys Pro Lys Ala Ala Glu Gly Leu Asp
50 55 60

Thr Gln Arg Phe Ser Gly Lys Arg Leu Gly Asp Thr Phe Val Leu Thr
65 70 75 80

Leu Ser Asp Phe Arg Arg Glu Asn Glu Gly Tyr Tyr Phe Cys Ser Ala
85 90 95

```
Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp Ile Tyr Ile Trp Ala Pro Leu Ala Gly Thr Cys Gly Val Leu Leu
                165                 170                 175

Leu Ser Leu Val Ile Thr Leu Tyr Cys
            180                 185


<210> SEQ ID NO 29
<211> LENGTH: 104
<212> TYPE: PRT
<213> ORGANISM: Artificial sequence
<220> FEATURE:
<223> OTHER INFORMATION: synthetic sequence

<400> SEQUENCE: 29

Leu Ser Tyr Arg Phe Lys Gln Gly Phe Arg Arg Ile Leu Leu Arg Pro
1               5                   10                  15

Ser Arg Arg Ile Arg Ser Gln Glu Pro Gly Ser Gly Pro Pro Glu Lys
            20                  25                  30

Thr Glu Glu Glu Glu Asp Glu Glu Glu Glu Glu Arg Arg Glu Glu Glu
        35                  40                  45

Glu Arg Arg Met Gln Arg Gly Gln Glu Met Asn Gly Arg Leu Ser Gln
    50                  55                  60

Ile Ala Gln Ala Gly Thr Ser Gly Gln Gln Pro Arg Pro Cys Thr Gly
65                  70                  75                  80

Thr Ala Lys Glu Gln Gln Leu Leu Pro Gln Glu Ala Thr Ala Gly Asp
                85                  90                  95

Lys Ala Ser Thr Leu Ser His Leu
            100


<210> SEQ ID NO 30
<211> LENGTH: 10
<212> TYPE: PRT
<213> ORGANISM: Artificial sequence
<220> FEATURE:
<223> OTHER INFORMATION: synthetic sequence

<400> SEQUENCE: 30

Cys Gln Asp Ser Glu Thr Arg Thr Phe Tyr
1               5                   10


<210> SEQ ID NO 31
<211> LENGTH: 21
<212> TYPE: PRT
<213> ORGANISM: Artificial sequence
<220> FEATURE:
<223> OTHER INFORMATION: synthetic sequence

<400> SEQUENCE: 31

Thr Ala Leu Ile Ile Leu Val Gly Ile Gly Ala Asp Asp Ala Phe Val
1               5                   10                  15

Leu Cys Asp Val Trp
            20
```

<210> SEQ ID NO 32
<211> LENGTH: 21
<212> TYPE: PRT
<213> ORGANISM: Artificial sequence
<220> FEATURE:
<223> OTHER INFORMATION: synthetic sequence

<400> SEQUENCE: 32

Phe Gly Met Val Leu Ala Ile Gly Leu Leu Val Asp Asp Ala Ile Val
1 5 10 15

Val Val Glu Asn Val
20

<210> SEQ ID NO 33
<211> LENGTH: 21
<212> TYPE: PRT
<213> ORGANISM: Artificial sequence
<220> FEATURE:
<223> OTHER INFORMATION: synthetic sequence

<400> SEQUENCE: 33

Val Leu Pro Phe Leu Ala Leu Gly Val Gly Val Asp Asp Val Gly Leu
1 5 10 15

Leu Ala His Ala Phe
20

<210> SEQ ID NO 34
<211> LENGTH: 21
<212> TYPE: PRT
<213> ORGANISM: Artificial sequence
<220> FEATURE:
<223> OTHER INFORMATION: synthetic sequence

<400> SEQUENCE: 34

Val Ile Pro Phe Leu Val Leu Ala Val Gly Val Asp Asn Ile Phe Ile
1 5 10 15

Leu Val Gln Thr Tyr
20

<210> SEQ ID NO 35
<211> LENGTH: 20
<212> TYPE: PRT
<213> ORGANISM: Artificial sequence
<220> FEATURE:
<223> OTHER INFORMATION: synthetic sequence

<400> SEQUENCE: 35

Val Gly Leu Leu Thr Thr Ile Gly Leu Ser Ala Lys Asn Ala Ile Leu
1 5 10 15

Ile Val Glu Phe
20

<210> SEQ ID NO 36
<211> LENGTH: 21
<212> TYPE: PRT
<213> ORGANISM: Artificial sequence
<220> FEATURE:
<223> OTHER INFORMATION: synthetic sequence

<400> SEQUENCE: 36

Val Thr Ile Ser Val Ala Val Gly Leu Ser Val Asp Phe Ala Val His
1 5 10 15

Tyr Gly Val Ala Tyr
20

<210> SEQ ID NO 37
<211> LENGTH: 21
<212> TYPE: PRT
<213> ORGANISM: Artificial sequence
<220> FEATURE:
<223> OTHER INFORMATION: synthetic sequence

<400> SEQUENCE: 37

Val Ile Leu Ile Ala Ser Val Gly Ile Gly Val Glu Phe Thr Val His
1 5 10 15

Val Ala Leu Ala Phe
20

<210> SEQ ID NO 38
<211> LENGTH: 21
<212> TYPE: PRT
<213> ORGANISM: Artificial sequence
<220> FEATURE:
<223> OTHER INFORMATION: synthetic sequence

<400> SEQUENCE: 38

Val Asn Leu Val Met Ser Cys Gly Ile Ser Val Glu Phe Cys Ser His
1 5 10 15

Ile Thr Arg Ala Phe
20

<210> SEQ ID NO 39
<211> LENGTH: 5
<212> TYPE: PRT
<213> ORGANISM: Artificial Sequence
<220> FEATURE:
<223> OTHER INFORMATION: synthetic sequence

<400> SEQUENCE: 39

Gly Gly Gly Gly Ser
1 5

<210> SEQ ID NO 40
<211> LENGTH: 9
<212> TYPE: PRT
<213> ORGANISM: Artificial Sequence
<220> FEATURE:
<223> OTHER INFORMATION: synthetic sequence

<400> SEQUENCE: 40

Gly Gly Gly Gly Gly Gly Gly Gly Gly
1 5

<210> SEQ ID NO 41
<211> LENGTH: 9
<212> TYPE: PRT
<213> ORGANISM: Artificial Sequence
<220> FEATURE:
<223> OTHER INFORMATION: synthetic sequence

<400> SEQUENCE: 41

Glu Glu Glu Glu Glu Glu Glu Glu Glu
1 5

<210> SEQ ID NO 42
<211> LENGTH: 9
<212> TYPE: PRT
<213> ORGANISM: Artificial Sequence
<220> FEATURE:
<223> OTHER INFORMATION: synthetic sequence

<400> SEQUENCE: 42

Ser Ser Ser Ser Ser Ser Ser Ser Ser
1 5

<210> SEQ ID NO 43
<211> LENGTH: 9
<212> TYPE: PRT
<213> ORGANISM: Artificial Sequence
<220> FEATURE:
<223> OTHER INFORMATION: synthetic sequence

<400> SEQUENCE: 43

Gly Gly Gly Gly Gly Cys Pro Pro Cys
1 5

<210> SEQ ID NO 44
<211> LENGTH: 15
<212> TYPE: PRT
<213> ORGANISM: Artificial Sequence
<220> FEATURE:
<223> OTHER INFORMATION: synthetic sequence

<400> SEQUENCE: 44

Gly Gly Gly Gly Ser Gly Gly Gly Gly Ser Gly Gly Gly Gly Ser
1 5 10 15

<210> SEQ ID NO 45
<211> LENGTH: 13
<212> TYPE: PRT
<213> ORGANISM: Artificial Sequence
<220> FEATURE:
<223> OTHER INFORMATION: synthetic sequence

<400> SEQUENCE: 45

Ser Cys Val Pro Leu Met Arg Cys Gly Gly Cys Cys Asn
1 5 10

<210> SEQ ID NO 46
<211> LENGTH: 14
<212> TYPE: PRT
<213> ORGANISM: Artificial Sequence
<220> FEATURE:
<223> OTHER INFORMATION: synthetic sequence

<400> SEQUENCE: 46

Pro Ser Cys Val Pro Leu Met Arg Cys Gly Gly Cys Cys Asn
1 5 10

<210> SEQ ID NO 47
<211> LENGTH: 9
<212> TYPE: PRT
<213> ORGANISM: Artificial Sequence
<220> FEATURE:
<223> OTHER INFORMATION: synthetic sequence

<400> SEQUENCE: 47

Gly Asp Leu Ile Tyr Arg Asn Gln Lys
1 5

<210> SEQ ID NO 48
<211> LENGTH: 23
<212> TYPE: PRT
<213> ORGANISM: Artificial Sequence
<220> FEATURE:
<223> OTHER INFORMATION: synthetic sequence

<400> SEQUENCE: 48

```
Gly Gly Gly Gly Gly Gly Gly Gly Gly Pro Ser Cys Val Pro Leu Met
1               5                   10                  15

Arg Cys Gly Gly Cys Cys Asn
            20


<210> SEQ ID NO 49
<211> LENGTH: 14
<212> TYPE: PRT
<213> ORGANISM: Artificial Sequence
<220> FEATURE:
<223> OTHER INFORMATION: synthetic sequence

<400> SEQUENCE: 49

Gly Ser Thr Ser Gly Ser Gly Lys Ser Ser Glu Gly Lys Gly
1               5                   10
```